US006106821A

United States Patent [19]
Baker et al.

[11] Patent Number: 6,106,821
[45] Date of Patent: Aug. 22, 2000

[54] FLY ATTRACTANT COMPOSITIONS

[75] Inventors: Thomas C. Baker; Allard A. Cosse, both of Ames, Iowa

[73] Assignee: Iowa State University Research Foundation, Inc., Ames, Iowa

[21] Appl. No.: 08/894,893

[22] PCT Filed: Jan. 3, 1997

[86] PCT No.: PCT/US97/00031

§ 371 Date: Dec. 5, 1997

§ 102(e) Date: Dec. 5, 1997

[87] PCT Pub. No.: WO97/24034

PCT Pub. Date: Jul. 10, 1997

Related U.S. Application Data

[60] Provisional application No. 60/009,555, Jan. 3, 1996.
[51] Int. Cl.[7] .......................... A01N 59/00; A01N 37/02; A01N 31/02; A01N 43/38
[52] U.S. Cl. .............................. 424/84; 424/405; 424/43; 424/664; 424/710; 424/716; 424/719; 424/720; 424/721; 514/412; 514/517; 514/557; 514/558; 514/663; 514/706; 514/707; 514/712; 514/713; 514/730; 514/731; 514/944; 514/964; 514/957
[58] Field of Search ............................... 424/84, 405, 43, 424/664, 710, 716, 719–721; 514/183, 210, 212, 218, 241, 247, 277, 359, 412, 517, 557, 558, 663, 706–707, 712–713, 730–731, 944, 964, 957

[56] References Cited

U.S. PATENT DOCUMENTS 3,996,349  12/1976  Mulla et al. ............................... 424/84

FOREIGN PATENT DOCUMENTS

WO 94/27441  12/1994  WIPO .

OTHER PUBLICATIONS

Baker et al., "Identification and Bioassay of Sex Pheromone Components of Carob Moth", *Journal of Chemical Ecology*, 17, pp. 1973–1987 (1991).
Baumgartner, "The housefly, *Musca domestica*, in Central Peru: ecological studies of medical importance," *Revta. Bras. Ent.*, 32, pp. 455–463 (1988).
Brown et al., "Chemical Attractants for the Adult House Fly", *Journal of Economic Entomology*, 54, pp. 670–674 (1961).
Browne, "The Use of Pheromones and Other Attractants in House Fly Control"; Ecogen, Inc.; Langhorne, PA; pp. 531–537 (1990).
Campbell, "The economics of the fly problem", University of Nebraska, West Central Research and Extension Center, North Platte, NE, pp. 34–39 (1993).
Chen et al., "Headspace Analysis of Malodorous Compounds from Swine Wastewater Under Aerobic Treatment", *Biosource Techn.*, 49, pp. 83–87, (1994).
Chen et al., "Concentrations of Malodorous Compounds in Swine Wastes During Storage", *J. Environ. Sci. Health*, A29, pp. 83–98 (1994).
Coppedge et al., "Field Comparisons of Liver and a New Chemical Mixture as Attractants for the Screwworm Fly", *Environmental Entomology*, 6, pp. 66–68 (1977).
Cork, "Identification of electrophysiologically–active compounds for New World screwworm, *Cochliomyia hominivorax*, in larval wound fluid", *Medical and Veterinary Entomology*, 8, pp. 151–159 (1994).
Cosse et al., "Electroantennographic and Coupled Gas Chromatographic–electroantennographic Responses of the Mediterranean Fruit Fly, *Ceratitis capitata*, to Male–Produced Volatiles and Mango Odor", *Journal of Chemical Ecology*, 21, pp. 1823–1836 (1995).
Cosse et al., "House Flies and Pig Manure Volatiles: Wind Tunnel Behavioral Studies and Electrophysiological Evaluations", *J. Agric. Entomol.*, 13, pp. 301–317 (1996).
Cosse et al., "Identification of volatile compounds from fungus–infected date fruit that stimulate upwind flight in female *Ectomyelois ceratoniae*" *Entomol.exp.appl.*, 72, pp. 233–238 (1994).
Den Otter et al., "Responses of individual antennal olfactory cells of tsetse flies (*Glossina m.morsitans*) to phenols from cattle urine", *Physiological Entomology*, 18, pp. 43–49 (1993).
Den Otter, "Olfactory responses of tsetse flies to phenols from buffalo urine", *Physiological Entomology*, 16, pp. 401–410 (1991).
Ephrussi et al., "A technique of Transplantation for Drosophila", *Am. Nat.*, 70, pp. 218–225 (1936).
Frishman et al., "Olfactory Responses of the Face Fly *Musca autumnalis* De Geer and the Housefly", *Cornell Experiment Station Memoir 394*, pp. 1–65 (1966).
Greenberg, "Flies and disease." *Princeton University Press, Princeton New York*, I, p. 856 (1973).
Holmqvist et al., "A visually evoked escape response of the housefly", *J. Comp. Physiol.* A16, pp. 451–459 (1991).
Künast et al., "Vergleichende Laboruntersuchungen über Lockstoffe und Köder bei der Stubenfliege (*Musca domentica L.*)", 54, pp. 131–135 (1981).
Larsen et al., "Olfactory and Oviposition Responses of the House Fly to Domestic Manures, with Notes on an Autogenous Strain", *Journal of Economic Entomology*, 59, pp. 610–614 (1966).

(List continued on next page.)

*Primary Examiner*—John Pak
*Attorney, Agent, or Firm*—Mueting, Raasch & Gebhardt, P.A.

[57] ABSTRACT

The invention relates to fly attractant compositions that comprise at least one volatile short chain carboxylic acid, at least one organic sulfide and at least one nitrogen heterocycle. In a preferred embodiment the composition additionally comprises at least one ammonia-releasing compound. In a particularly preferred example, the composition is preparable by combining, for example, the carboxylic acid, the organic sulfide and the nitrogen heterocycle. The invention also relates to an insect trap comprising a means for retaining flies and an insect attractant composition of this invention. The trap is useful in commercial, residential and livestock facilities.

54 Claims, 5 Drawing Sheets

OTHER PUBLICATIONS

Mackley et al., "Swormlure–4: A New Formulation of the Swormlure–2 Mixture as an Attractant for Adult Screwworms, *Cochliomyia hominivorax* (Diptera: Calliphoridae)", *Journal of Economic Entomology,* 77, pp. 1264–1268 (1984).

Miller et al., "Sustained–Flight Tunnel for Measuring Insect Responses to Wind–Borne Sex Pheromones", *J. Chem. Ecol.,* 4, pp. 187–198 (1978).

Mulla et al., "Chemical attractants tested against the Australian bush fly, *Musca vetustissima* (Diptera: Muscidae).", *J. Chem. ecol.,* 12, pp. 261–270 (1986).

Mulla et al., "Attractants for Synanthropic Flies: Chemical Attractants for Domestic Flies", *Journal of Economic Entomology,* 70, pp. 644–648 (1977).

Meyer et al., "House Fly (Diptera: Muscidae) Resistance to Permethrin on Southern California Dairies", *J. Econ. Entomol.,* 80, pp. 636–640 (1987).

O'Neill et al., "A Review of the Control of Odour Nuisance from Livestock Buildings: Part 3, Properties of the Odorous Substances which have been Identified in Livestock Wastes or in the Air around them", *J. agric. Engng Res.,* 53, pp. 23–50 (1992).

Peterson et al., "Attraction of Non–Target Organisms to SWASS", *Environ. Entomol.,* 10, pp. 511–516 (1981).

Ridgeway et al., "Behavior and Modifying Chemicals for Insect Management"; Marcel Dekker, Inc.; New York, New York (1990).

Saini et al., "Olfactory Sensitivity of Tsetse to Phenolic Kairomones", *Insect Sci. Applic.,* 13, pp. 95–104 (1992).

Schofield et al., "Electroantennogram responses of the stable fly, *Stomoxys calcitrans,* to components of host odour", *Physiological Entomology,* 20, pp. 273–280 (1995).

Scott et al., "Rapid Development of High–level Permethrin Resistance in a Field–collected Strain of the House Fly (Dipteria: Muscidae) Under Laboratory Selection", *J. Econ. Entomol.,* 78, pp. 316–319 (1985).

Skoda and Thomas, "Proceeding of a symposium: Rural flies in the urban environment?", *University of Nebraska–Lincoln, Res. Bull.,* (1993).

Spoelstra, "Origin of objectionable odorous components in piggery wastes and the possibility of applying indicator components for studying odour development", *Agriculture and Environment,* 5, pp. 241–260 (1980).

West, *The Housefly,* Comstock Publishing Co., Ithaca, New York, p. 584 (1951).

West & Peters, "An annotated bibliography–of *Musca domestica* Linnaeus," *Dawsons of Pall Mall,* London, p. 743 (1973).

Warnes et al., "Electroantennogram responses of the stable fly, *Stomoxys calcitrans,* to carbon dioxide and other odours", *Physiological Entomology,* 11, pp. 469–473 (1986).

Yasuhara et al., "Identification of Odorous Compounds in Fresh and Rotten Swine Manure", *Agric. Biol. Chem.,* 48, pp. 3001–3010 (1984).

Yasuhara et al., "Volatile and Odorous Components in Solid Swine Manure", *Agric. Biol. Chem.,* 43, pp. 313–316 (1979).

Sokal & Rohlf 1981. *Biometry.* W.H. Freeman & Company, San Francisco, CA, pp. 859.

C. M. Jones et al., "A Chemical Attractant for Screwworm Flies," *J. Econ. Entomol.,* 69: 389–391 (1976).

FLY ATTRACTANT COMPOSITIONS

This application is a 371 of PCT/US97/00031, filed on Jan. 3, 1997 and claims priority from a provisional patent application filed on Jan. 3, 1996 entitled "Novel House Fly Attractant" and assigned Provisional Ser. No. 60/009,555.

FIELD OF THE INVENTION

This invention relates to the field of insect attractants and in particular this invention relates to compositions and methods for preparing and using fly attractants.

BACKGROUND OF THE INVENTION

The house fly (Musca domestica L.) enjoys a cosmopolitan distribution. The enormous potential that this species possesses for pathogen transmission is well documented (Greenberg 1973, *Flies and disease*. Vol. I. Princeton University Press, Princeton N.Y., 856 pp. and West & Peters 1973, *An annotated bibliography of Musca domestica Linnaeus*. Dawsons of Pall Mall, London, 743 pp.). In addition to transmitting disease, the house fly is a major pest in or around livestock, swine, and poultry facilities (West, L.S., 1951, *The housefly*. Comstock Publishing Company, Ithaca, N.Y., 584 pp.). Heavy fly populations not only can cause actual economic losses in production to various classes of livestock but also can cause other economic losses. For example, livestock production facilities may be cited as a nuisance to surrounding residents as a result of flies, odor, and dust with resulting fines, attorney fees and settlement costs. (Campbell 1993. "The economics of the fly problem," pp. 34–39. In G. D. Thomas & S. R. Skoda. [Eds.], *Proceeding of a symposium: Rural flies in the urban environment?* University of Nebraska-Lincoln, Res. Bull. 317, 97 pp.).

Insecticides have been used as the primary method for fly control for the last 100 years and are still widely employed today. In spite of the large numbers of chemical products available, heavy fly populations are still present at livestock installations and the flies can disperse into urban areas (Thomas & Skoda 1993. supra). Many house fly control failures have been attributed to insecticide resistance (Meyer et al. 1987 *J. Econ. Entomol.* 80:636–640, Scott & Georghiou 1985, *J. Econ. Entomol.* 78:319–326).

One of the alternative control methods for house flies is attractants which can be deployed in the domestic and feedlot environment. However, existing commercial house fly attractant baits have shown mixed results (Browne 1990. "The use of pheromones and other attractants in house fly control." pp. 531–537. In L. R. Ridgway, R. M. Silverstein & M. N. Inscoe [Eds.], *Behavior-modifying chemicals for insect management*. Marchel Dekker, Inc., 761 pp.). Studies on attractants for the house fly are not new and have focused on evaluating the attractancy of single compounds or complex odorant mixtures in olfactometers, small rooms, and the field (West & Peters 1973, supra and references therein). These studies have demonstrated that mixtures are more attractive than single chemicals (Brown et al. 1961. *J. Econ. Entomol.* 54:670–674), Mulla et al., 1977. *J Econ. Entomol.* 70:644–648, Künast & Günzrodt, 1981. *Anz. Schadlingskde. Pflanzenschutz Umweltschutz* 54:131–135). House flies can be attracted to single odor sources such as indole, 3-methylindole, or butanoic acid in the field (Brown et al. 1961, *J Econ. Entomol.* 54:670–674; Frishman & Matthysse 1966, "Olfactory responses of the face fly *Musca autumnalis* De Geer and the house fly *Musca domestica* Linn." In *Memoirs Cornell University Agricultural Experiment Station*, 496. Cornell University, Ithaca, N.Y.; and Mulla et al. 1977, supra). However, the most effective attractants for house flies appear to be natural products, and especially effective are the products of putrefaction and fermentation, the sources of which can serve as oviposition sites and food sources. Dairy products and sugar-containing substances also are considered effective attractants (Künast & Günzrodt 1981 supra). These sources are generally malodorous and are therefore not acceptable as commercial or residential fly attractants.

Manure and spilled feed are the principal breeding media for the house fly (Skoda & Thomas 1993. "Breeding sites of stable flies and house flies," p. 61–67. In G. D. Thomas & S. R. Skoda. [Eds.], *Proceedings of a symposium: Rural flies in the urban environment?* University of Nebraska-Lincoln, Res. Bull. 317, 97 pp.). Larsen et al. (1966. *J Econ. Entomol.* 59:610–615) demonstrated that odor taken from air that has passed through a mixture of water and pig manure was attractive to house flies in an olfactometer, and that of eight different types of manure tested, pig manure was the most favorable site for oviposition.

Considerable effort has been expended to identify the compounds emanating from livestock manure. In pig manure, at least 140 different volatile compounds and gasses have been identified (Yashuhara & Fuwa 1979. *Agric. Biol. Chem.* 43:313–316;, Spoelstra 1980, *Agric. Environ.* 5:241–260; Yashuhara et al. 1984, *Agric. Biol. Chem.* 48:3001–3010; O'Neill & Phillips 1992, *J. Agric. Engng. Res.* 53:23–50; and, Chen et al., 1994, *Biosource Techn.* 49:83–87).

Chemical attractants have been used to attract other insects. For example, Jones et al. and others identified a chemical attractant for the screwworm (*Cochilomyia hominivorax*), swormlure-4. This attractant is a synthetic blend of compounds derived from decomposing liver and includes 2-butanol, 2-methyl-2-propanol, dimethyl disulfide, acetic acid, butanoic acid, pentanoic acid, phenol, p-cresol, benzoic acid, and indole (*J. Econ. Entomol.* 69:389–391, 1976; Coppedge et al. 1977, *Environ Entomol.* 6:66–68; and, Mackley & Brown. 1984, *J. Econ. Entomol* 77:1264–1268). Research performed on nontarget insects attracted to an older formulation of swormlure-4, swormlure-2 (Coppedge et al. 1977, supra), showed that of the 168 collected insect species (totaling 4,640 insects), only 4% were in the family Muscidae of which the housefly is but one of hundreds of species (Peterson et al. 1981, *Environ. Entomol.* 10:511–516).

There is a paucity of literature regarding the actual volatile compounds in pig manure that are responsible for attracting house flies. Chemical attractants that are commercially available have met with only limited success. New chemical attractants are needed to control house fly infestation.

SUMMARY OF THE INVENTION

This invention relates to fly attractant compositions, traps including the fly attractant compositions of this invention, and methods for attracting flies using the compositions of this invention.

In a first aspect of this invention a fly attractant composition is disclosed that comprises at least one ammonia-releasing compound, at least one volatile short chain carboxylic acid, at least one organic sulfide, and at least one nitrogen heterocycle. In one embodiment, the ammonia-releasing compound is selected from a group of ammonium carbonate, ammonium chloride, ammonium gas and ammonium sulfate, the volatile short chain carboxylic acid is preferably selected from the group of volatile short chain carboxylic acids naturally occurring in pig or cow manure and in one embodiment the volatile short chain carboxylic acid is selected from the group of straight or methyl-branched aliphatic carboxylic acids containing 2–5 carbon atoms. In a particularly preferred embodiment, the volatile short chain carboxylic acid is selected from the group of butanoic acid and 3-methyl butanoic acid. Preferably, the organic sulfide is selected from a group of organic sulfides naturally occurring in pig or cow manure and more preferably, the organic sulfide is selected from the group of dimethyl disulfide, dimethyl trisulfide and dimethyl tetrasulfide. Preferably, the nitrogen heterocycle is selected from a group of nitrogen heterocycles naturally occurring in pig or cow manure and more preferably the nitrogen heterocycles are selected from the group of indole and 3-methyl indole. In a particularly preferred combination, the fly attractant composition comprises at least one ammonia-releasing compound, butanoic acid, dimethyltrisulfide and indole.

In addition, the fly attractant composition of this invention can further comprises at least one additional component selected from the group of volatile aromatic-containing alcohols and volatile amines naturally occurring in pig or cow manure. Preferably, the at least one additional component is selected from the group of phenol, benzeneethanol, and trimethylamine. In another preferred embodiment the fly attractant composition additionally includes an insecticide.

In one embodiment, the fly attractant compositions of this invention are provided in a sustained release dispenser and preferably the sustained release dispenser is a pump, including a pump atomizer or for example, a metered aerosol device that discharges onto a substrate, a gel or a membrane.

In another embodiment the fly attractant composition of this invention is capable of stimulating an electroantennogram response from a fly antenna and still more preferably, the composition is capable of stimulating a volatile plume-oriented upwind flight in flies released in a wind tunnel having a wind velocity of about 50 cm/second.

In another aspect of this invention, the invention relates to a fly trap comprising means to retain flies within the trap and a fly attractant composition comprising at least one ammonia-releasing compound, at least one volatile short chain carboxylic acid, at least one organic sulfide, and at least one nitrogen heterocycle. In one embodiment, the ammonia-releasing compound is selected from a group of ammonium carbonate, ammonium chloride, ammonia gas and ammonium sulfate, the volatile short chain carboxylic acid is selected from the group of butanoic acid and 3-methyl butanoic acid, the organic sulfide is selected from the group of dimethyl disulfide, dimethyl trisulfide and dimethyl tetrasulfide and the nitrogen heterocycle is selected from the group of indole and 3-methyl indole. In a preferred embodiment the trap includes an attractant composition comprising butanoic acid, dimethyltrisulfide and indole.

In a preferred embodiment, the trap further comprises at least one additional component selected from the group of volatile aromatic-containing alcohols and volatile amines naturally occurring in pig or cow manure. Preferably the at least one additional component is selected from the group of phenol, benzeneethanol, and trimethylamine.

Preferably, the attractant composition in the trap is provided in a sustained release dispenser and preferably the sustained release dispenser is a pump, a gel or a membrane.

In a preferred embodiment the trap comprising the attractants of this invention include a means to retain flies and in particular the means to retain flies comprises a tacky surface, an insecticide, a trap box, electrocution, or liquid. In one embodiment, the trap additionally comprises a heat stimulus or a visual stimulus. In a preferred embodiment, the visual stimuli is light and in one embodiment, the visual stimuli is UV light.

Preferably the trap attracts house flies, stable flies, face flies or flesh flies.

In another aspect of this invention, the invention relates to a method for attracting flies comprising the steps of preparing a composition comprising at least one ammonia-releasing compound, at least one volatile short chain carboxylic acid, at least one organic sulfide, and at least one nitrogen heterocycle; and placing the composition in an area where flies are present. The method can also comprise the step of combining the composition with a means for retaining flies. In a preferred embodiment, the ammonia-releasing compound is selected from a group of ammonium carbonate, ammonium chloride, ammonia gas and ammonium sulfate; the volatile short chain carboxylic acid is selected from the group of butanoic acid and 3-methyl butanoic acid; the organic sulfide is selected from the group of dimethyl disulfide, dimethyl trisulfide and dimethyl tetrasulfide; and, the nitrogen heterocycle is selected from the group of indole and 3-methyl indole. In a particularly preferred embodiment the composition comprises an ammonia-releasing compound, butanoic acid, dimethyltrisulfide and indole. The composition in the method also preferably comprises at least one additional component selected from the group of volatile aromatic-containing alcohols and volatile amines naturally occurring in pig or cow manure, including, but not limited to phenol, benzeneethanol, and trimethylamine.

In a preferred embodiment of the method, the positioning step takes place in a livestock facility, in a residence, or in a commercial facility, including, but not limited to a restaurant, a slaughterhouse, a school or a hospital.

Preferably, the attractant composition is provided in a sustained release dispenser and preferred sustained release dispensers include a pump, a gel or a membrane. Preferred means for retaining flies in this aspect include a tacky surface, an insecticide, a trap box, electrocution, or liquid.

In another aspect of this invention a fly attractant composition is disclosed that comprises at least one volatile short chain carboxylic acid, at least one organic sulfide, and at least one nitrogen heterocycle wherein the volatile short chain carboxylic acid, the organic sulfide and the nitrogen heterocycle are naturally occurring in pig or cow manure. In a preferred embodiment of this composition, the volatile short chain carboxylic acid is selected from the group of butanoic acid and 3-methyl butanoic acid; the organic sulfide is selected from the group of dimethyl di sulfide, dimethyl trisulfide and dimethyl tetrasulfide; and, the nitrogen heterocycle is selected from the group of indole and 3-methyl indole. The composition can further comprise at least one of the following chemicals selected from the group of benzeneethanol, phenol and trimethylamine. The composition is preferably provided in a sustained release dispenser and in a preferred embodiment, the sustained release dispenser is a pump.

In yet another aspect of this invention a fly attractant composition is disclosed that is preparable by combining at least one ammonia-releasing compound, at least one volatile short chain carboxylic acid, at least one organic sulfide, and at least one nitrogen heterocycle wherein the composition is capable of stimulating an electroantennogram response from a fly antenna and still more preferably, the composition is capable of stimulating a volatile plume-oriented upwind flights in flies released in a wind tunnel having a wind velocity of about 50 cm/second.

DETAILED DESCRIPTION OF THE PREFERRED EMBODIMENTS

Figure 1:
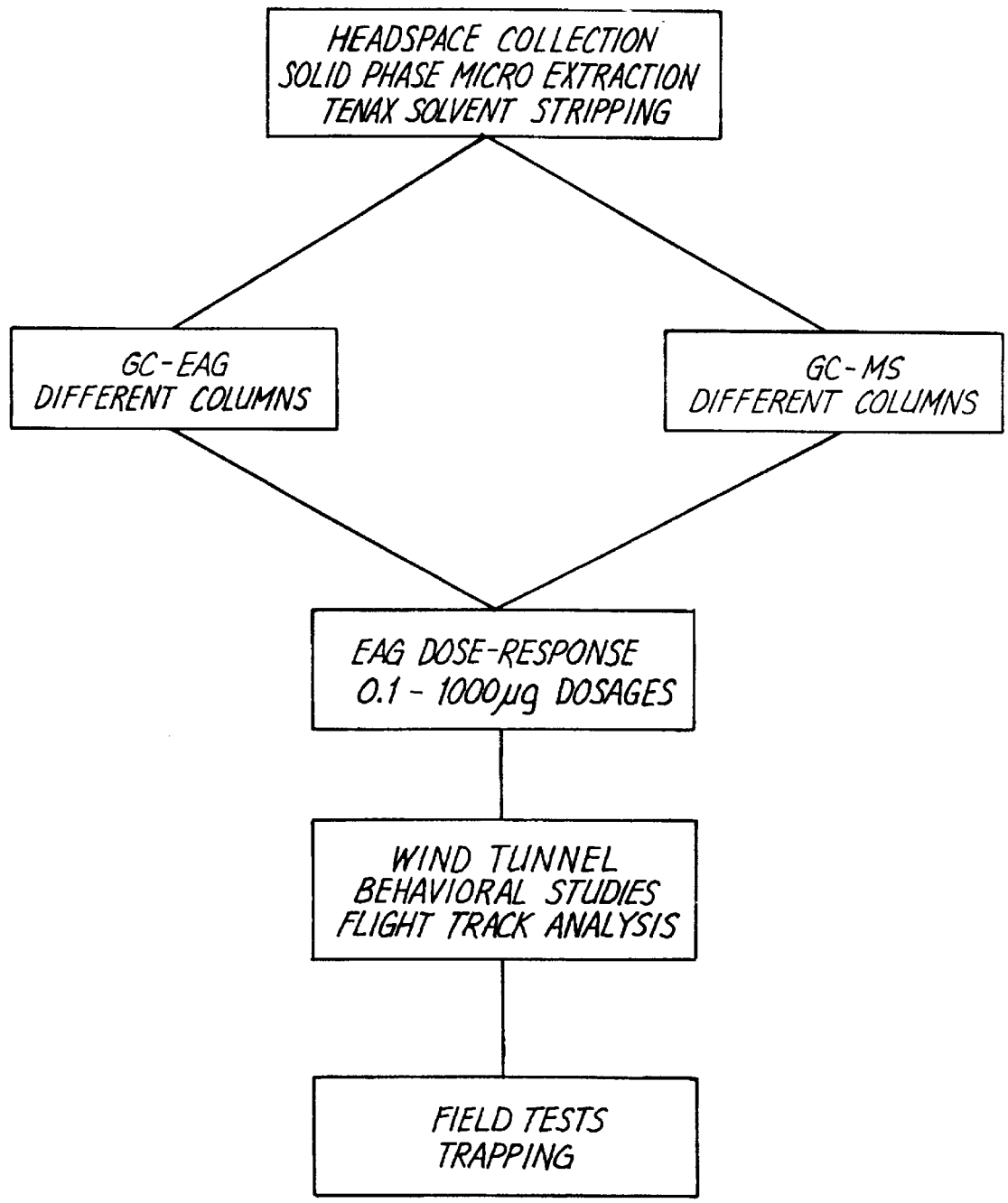
FIG. 1 provides a preferred method for identifying novel chemical attractant compositions.

This invention relates to novel chemical attractant compositions prepared from chemicals originally identified in livestock manure, putrefication and/or fermentation products. In addition, the compositions of this invention include other chemicals with properties similar to those of the compounds identified in livestock manure that also have fly attractant properties including electroantennogram-stimulating activity and the ability to stimulate upwind flight activity in a wind tunnel bioassay, as described herein. In the present study novel compositions are disclosed as attractants for flies and in a preferred embodiment, attractants are identified for the common house fly (Musca domestica).

As used herein, the term "attractant" refers to any composition, chemical or other stimuli that draws an insect toward a particular location. Attractants include thermostimuli, mechanostimuli (e.g. airborne sound waves, or substrate borne pressure waves), electromagnetic stimuli (including visual stimuli such as patterns, objects, color, light), and chemical stimuli including odors. A chemical attractant can be an individual compound or a composition, including more than one compound, that either directly or indirectly elicits a positive directional response from the insect, drawing the insect resulting in the arrivint at or near the source of the stimuli.

As used herein, the term "manure" refers to excrement from livestock and refers to a combination of urine and solid excrement. The term "naturally occurring in pig or cow manure" refers to compounds used to prepare the compositions of this invention that can generally be found in pig or cow manure from pigs or cows that have been fed standard livestock facility pig or cow feed.

As used herein the term "volatile" refers to compounds and compositions that can be readily vaporized at ambient temperature and can be detected by GC/MS.

In one embodiment of this invention, the invention relates to a fly attractant composition comprising at least one volatile short chain carboxylic acid, at least one organic sulfide, and at least one nitrogen heterocycle containing compound.

Volatile short chain carboxylic acids include carboxylic acids having 1–8 carbon atoms and preferred short chain carboxylic acids include those carboxylic acids having 2–5 carbon atoms. Preferably the carboxylic acids used in the composition of this invention are those that are naturally occurring volatiles present in livestock waste, particularly pig and/or cow manure (see O'Neill and Phillips, supra). These include methanoic acid, ethanoic acid, propanoic acid, butanoic acid, 2-methylpropanoic acid, pentanoic acid, 3-methylbutanoic acid, 2-methylbutanoic acid, 2-methyl-2-butanoic acid, hexanoic acid, 4-methylpentanoic acid, 2-methylpentanoic acid, heptanoic acid, octanoic acid, benzoic acid, phenylethanoic acid, and 3-phenylpropanoic acid. Also, in a preferred embodiment the volatile short chain carboxylic acids are either straight or methyl branched aliphatic carboxylic acids. Preferred carboxylic acids include butanoic acid and 3-methyl butanoic acid.

Volatile organic sulfides preferably refer to those organic sulfides that are naturally occurring in livestock waste, particularly pig and/or cow manure (see O'Neill and Phillips, supra) and preferred volatile organic sulfides include, but are not limited to, dimethyl disulfide, dimethyl trisulfide and dimethyl tetrasulfide. Other sulfides contemplated in this invention, include, but are not limited to methylthiomethane, dimethylsulfide, diethylsulfide, diethyldisulfide, dipropyldisulfide, methylpropyldisulfide, diphenylsulfide, 3,5-dimethyl-1,2,4-trithiolane, 3-methyl-5-propyl-1,2,4-trithiolane, and the like. The term "organic" is used herein to refer to sulfides that contain carbon compounds and preferably sulfides that include hydrogen atoms bonded to at least one carbon atom In addition, the preferred composition of this invention includes volatile nitrogen heterocycle-containing compounds. Again, preferred nitrogen heterocycle-containing compounds include those volatile nitrogen heterocycle-containing compounds present in livestock waste, particularly pig and/or cow manure (see O'Neill and Phillips, supra). Exemplary nitrogen heterocycles contemplated in this invention include, but are not limited to, indole, skatole (3-methylindole), pyridine, 3-aminopyridine, (2)-methylpyrazine, methylpyrazine, trimethylpyrazine and tetramethylpyrazine. Preferred nitrogen heterocycle-containing compounds include, but are not limited to indole and 3-methyl indole.

Optionally, the fly attractant compositions of this invention also include aromatic alcohols such as phenol, 4-methylphenol, 3-methylphenol, benzeneethanol, 4-ethylphenol and the like. Preferred aromatic alcohols include phenol and benzeneethanol.

Other optional compounds that can be added to the compositions of this invention include trimethylamine and other amines including, but not limited to methylamine, triethylamine, aminoethane, and the like.

A preferred schematic illustrating the method steps involved in identifying the preferred compositions of this invention is provided in FIG. 1.

Pig manure volatiles were initially analyzed by coupled gas chromatographic-electroantennographic (GC-EAG) and coupled GC-mass spectrometry (GC-MS) assays to isolate and identify those compounds in the headspace of pig manure that are biologically active. The GC-EAG system was used to separate compounds emitted from a natural fly attractant, here pig manure, and the natural attractant and components of the attractant were analyzed for their neurophysiological-stimulating activity. The system separates compounds emitted from the natural material while neurophysiologically assessing the compounds for their activity on the fly antenna. The degree of neuronal activity registered on an insect antenna through EAG is strongly correlated with behavior activity (Cossé et al. 1994, *J. Chem. Ecol.* 21:1823–1836 and and Cossé et al. 1995, *Entomol. Exp. Appl.* 72:233–238). The same array of volatile compounds from the natural material was injected onto a coupled gas chromatographic/mass spectrometric system (GC-MS) to identify the EAG-active volatile compounds. Preferred methods for assessing the volatiles in pig manure are provided in Example 1 and preferred methods for performing GC-EAG are provided in Example 2.

The GC-EAG analyses demonstrated that female house fly antennae selectively responded to a number of compounds that were present in the headspace of pig manure (see Table 1 of Example 2). The compounds identified in Table 1 and included in this example include butanoic acid, 3-methylbutanoic acid, dimethyldisulfide, dimethyltrisulfide, dimethyltetrasulfide, phenol, indole, 3-methylindole (skatole), and benzeneethanol. These compounds have been identified in pig manure as reported in references related to livestock waste management (Yashuhara & Fuwa 1979 supra; Spoelstra 1980, *J. Agric. Environ.* 5:241–260; Yashuhara et al. 1984, supra; O'Neill & Philips 1992, *J. Agric. Engng. Res.* 53:23–50; and, Chen et al. 1994, *Bioresource Techn.* 49:83–84), and with the exception of benzeneethanol, are key components of the objectionable or malodorous nature of swine waste (Spoelstra 1980 supra, O'Neill & Phillips 1992 supra, Chen & Liao 1994, *J. Environ. Sci. Health* A29:83–98; and, Chen et al. 1994 supra).

Wind tunnel assays were used to verify the attractancy of the identified neurophysiologically active pig manure volatiles and permitted testing of various other compositions and optimization of the compositions by testing a variety of ratios of the compounds forming the attractant compositions of this invention. In these studies, flies were required to actively fly upwind in a plume of volatiles and land at the source over about 5 minutes. Preferred methods for performing the wind tunnel assays are provided in Example 3. In one example, the wind-tunnel behavioral assays identified at least two mixtures, one composition comprising seven EAG-active compounds (3-methylindole, butanoic acid, 3-methylbutanoic acid, dimethyltrisulfide, indole, benzeneethanol, and phenol) and a second composition comprising butanoic acid, 3-methylindole, and dimethyltrisulfide as compositions capable of attracting female flies at a rate similar to that of pig manure. The attractancy of any one individual EAG-active compound tested was not significantly greater than that of the control; however, the combined effect of the chemicals as a composition generated significant attractant activity.

Synthetic samples of the compounds can be tested as candidate synthetic attractant compositions using any of a variety of assays such as the wind tunnel bioassay or by trapping methods as provided in Example 6. Various blends, ratios and dosages of the compounds can be tested to identify a combination of compounds that would provide optimal attractancy of the flies in the upwind flight and landing test. Similarly, individual compounds can be tested at various dosages for their individual effects in stimulating fly antennae or in stimulating upwind flight activity in a wind tunnel bioassay and based on results of those studies of individual compounds, compounds can be used alone or in combination with other positively identified compounds. Maximizing attractancy while minimizing odor is important for the use of this composition in a domestic environment. Methods for testing various combinations to formulate the compositions of this invention can follow the methods disclosed by Cossé et al. (*J. Agric. Entomol.* 13(4): 301–317) in view of the present disclosure without undue experimentation.

Based on the wind tunnel tests, further testing was performed to determine whether a blend of fewer components could be used as provided in Example 4, Table 3. Results from these experiments demonstrated that blends containing butanoic acid, dimethyltrisulfide with either indole or 3-methylindole were good attractants. Since no difference between the two blends was detected, further experiments used blends containing indole since humans are less sensitive to indole as compared to 3-methylindole.

This invention also contemplates the use of at least one ammonia to enhance the attractancy of the composition of this invention. Therefore, in another embodiment of this invention, the invention relates to a composition comprising an ammonia-releasing compound and further preferably comprising at least one volatile short chain carboxylic acid such as butanoic acid, at least one organic sulfide, such as, for example, dimethyltrisulfide with at least one nitrogen heterocycle such as, for example, indole or 3-methylindole. The effect of ammonia on the attractancy of the compositions of this invention was assessed in wind tunnel assays using, for example, the protocols of Example 3. The results of several experiments are provided in Tables 4–6 of Example 5. Preferably the ammonia-releasing compound is a substance capable of releasing volatile ammonia into the surrounding air. A variety of ammonia-releasing compounds can be used in this invention that produce ammonia volatiles including, but are not limited to, ammonium chloride, ammonium sulfate, ammonium carbonate salts, urea or free ammonia, such as ammonia gas, in solution.

Preferably the ammonia is provided from an aqueous solution containing less than a 5% solution of an ammonia-releasing compound and in a preferred embodiment, the ammonia-releasing compound is $(NH_4)_2CO_3$. In a particularly preferred embodiment a 2% solution of $(NH_4)_2CO_3$ was tested in combination with the compounds and the compositions contemplated in this invention. In a preferred embodiment a 2% solution of $(NH_4)_2CO_3$ was combined with butanoic acid, dimethyltrisulfide and indole. Other combinations tested are provided in Table 5 and 6 in Example 5. Those skilled in the art will recognize that various concentrations of $(NH_4)_2CO_3$ can be combined with various ratios and combinations of the volatile attractants of this invention and tested for their attractancy without undue experimentation. The attractancy of the three component blend doubled when a solution of about 2% $(NH_4)_2CO_3$ was added. Ammonia levels of less than a 5% solution of $(NH_4)_2CO_3$ are still acceptable for use in residential environments. Greater concentrations of ammonia-releasing compounds create unacceptable odors for closed residential environments. Greater concentrations of ammonia can be used in the compositions of this invention in areas with greater ventilation and the odor associated with ammonia is not as great an issue when the composition is used in livestock areas.

Further, the compositions of this invention containing at least one ammonia-releasing compound can also include aromatic-containing alcohols and/or amines, as discussed above.

Example 5 also provides several preferred methods for testing the attractants of this invention. As a comparison of the efficacy of the present invention with commercially available fly attractant products, a composition comprising equal portions of butanoic acid, 3-methylindole, dimethyltrisulfide and $(NH_4)_2CO_3$ was compared to a household trap-attractant kit ("Stick-A-Fly", Eaton & Co., Inc. Twinsburg, Ohio). The commercial test is roughly the equivalent of a sticky cardboard tube with visual cues including pictures of fly clusters that uses the house fly sex pheromone, (Z)-9-tricosene (Sex-A-Trax®, Eaton & Co. supra), formulated on blue-colored large-grain sugar. Comparative experiments were performed using the compositions of this invention employing identical traps, without bait and adding, in one example, a three component blend and $(NH_4)_2CO_3$, as outlined in a preferred method in Example 5. House fly trapping results were compared with the commercial product in two different settings: a laboratory and a natural household environment. The results indicated that during the first three hours of the experiments, traps with compositions repared according to this invention trapped flies while no flies were caught during the same period using the commercially available trap (see Example 5 and Tables 7 and 8). This indicated that house flies are more attracted to the synthetic mixture than to the sugar-pheromone baited trap.

Figure 5:
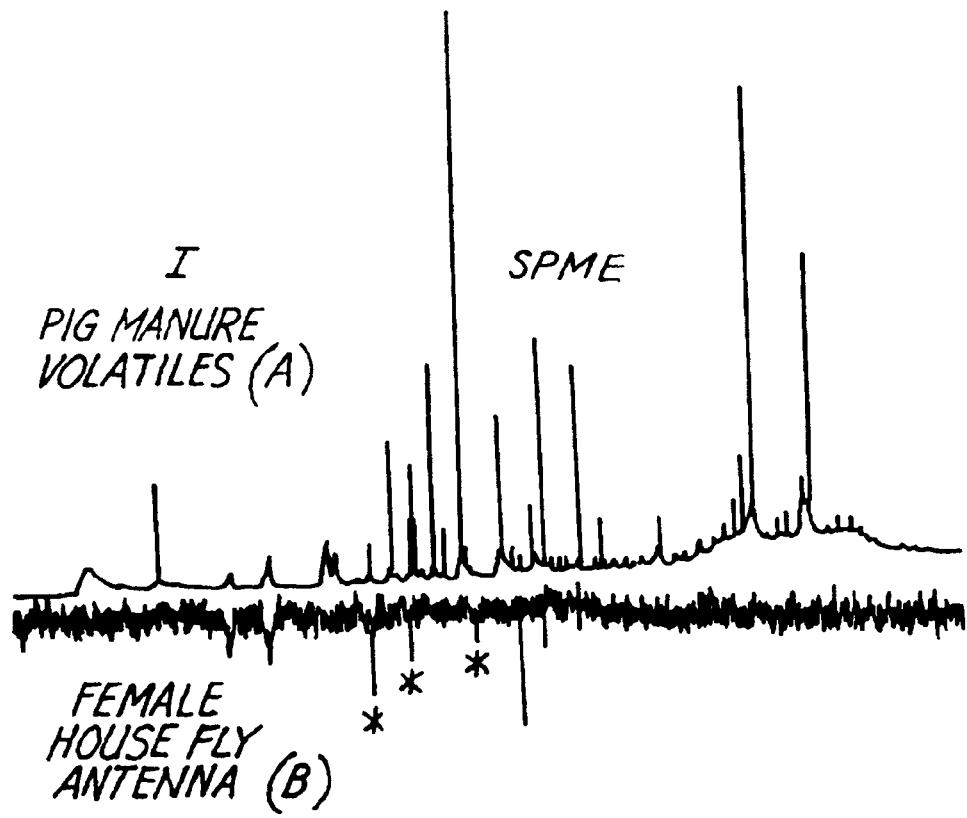
FIG. 5 provides two recorded gas chromatograms of pig manure volatiles collected by solid phase microextraction (A) and their corresponding simultaneously recorded electroantennograms from female house fly (I) and face fly (II) antennas (B). Based on the parameters of this study, electrophysiologically active compounds for the House fly and the Face fly antennae are labeled with an asterisk.
Figure 5:
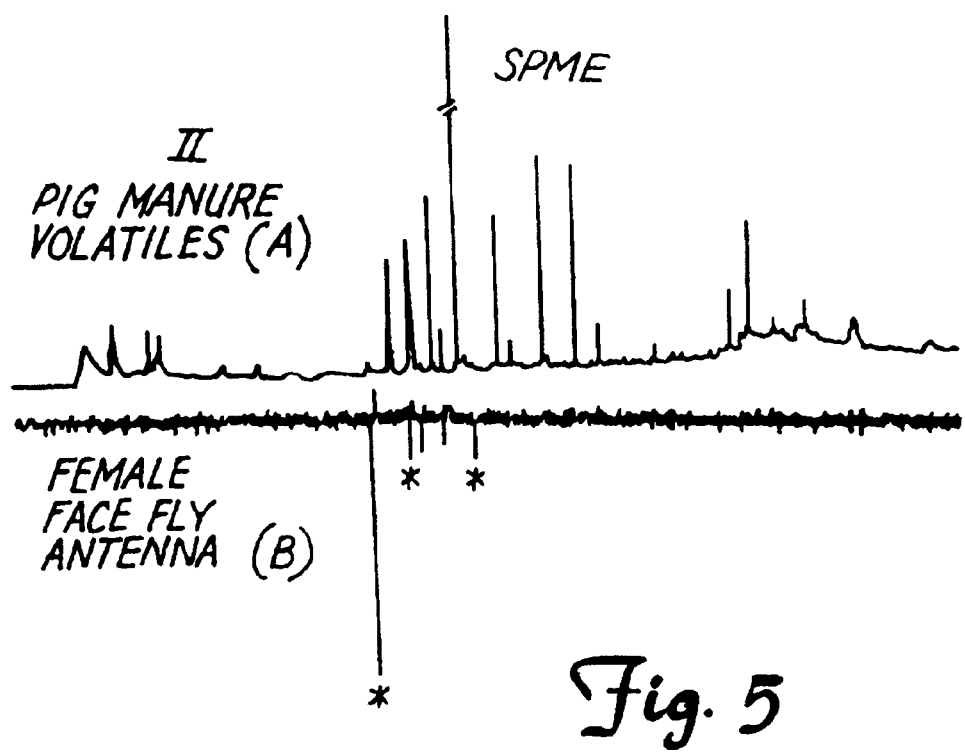

The invention is useful as an attractant for a variety of flies including house fly, stable flies (*Stomoxys calcitrans*), face flies (*Musca autumnalis*) and a variety of flying and crawling insects that can be found in and around livestock facilities. A composition of this invention comprising butanoic acid, dimethyltrisulfide, indole and $(NH_4)_2CO_3$ was also found useful for attracting flesh flies (those of the family Sarcophagidae), small house flies (*Fannia canicularis*), and blow flies (family of Calliphoridae) among other Diptera. FIG. 5 provides two recorded gas chromatograms of pig manure volatiles collected by solid phase microextraction (A) and their corresponding simultaneously recorded electroantennograms (B) from female House fly (I) and face fly (II) antennas (B) indicating that a preferred composition of this invention attracted both house flies and face flies.

The composition can be incorporated into traps for use inside or outside the home, in commercial facilities including restaurants, health care facilities, and animal care facilities. The invention is used in a preferred embodiment to attract flies in a residential setting. In another preferred embodiment, the invention is used to attract insects, preferably flying insects from livestock, including swine and poultry facilities.

The results of these studies identified at least nine compounds with EAG activity for male and female house fly antennae including butanoic acid, 3-methylbutanoic acid, dimethyldisulfide, dimethyltrisulfide, dimethyltetrasulfide, phenol, benzeneethanol, indole and 3-methylindole (skatole). All of these compounds, except benzeneethanol, are key components of the malodorous character of swine waste. To formulate a fly bait acceptable for human noses, the release rates of these compounds should be kept low but the product should still be capable of attracting flies. The wind tunnel bioassay allowed testing of dosages of individual and combinations of the volatiles from pig manure, including dosages that were below the level for human detection but which were capable of attracting flies in the wind tunnel and in domestic environments. Those skilled in the art will recognize that the wind tunnel bioassay also provides a ready format for assessing the compositions of this invention in combination with a variety of other compounds whether they be other volatiles, adjuvants or compounds to mask the odor of the volatiles.

The compositions of this invention can be combined with other stimuli to increase the attractancy of the composition, the potency of a fly attractant and the overall efficiency of an insect trap containing the composition of this invention. The composition of this invention can be used with one or more other stimuli such as heat stimuli, light stimuli, color or pattern stimuli and in combination with other chemical stimuli such as pheromones, other attractants and the like. Each of these combinations can be tested in the wind tunnel assay and/or in a fly trap setting such as described in Examples 3–5.

A variety of other chemicals, foods and compounds are known to attract flies including combinations of pig manure and cow manure, volatiles from cow manure alone, dried milk powder, molasses, Limburger cheese or volatile components from these substances. These products or volatiles from these products can be included in the composition of this invention. The various mixtures can be tested using the test regimes of this invention without undue experimentation.

The compounds can be further combined with various adjuvants to mask the offending odor from the attractant while retaining acceptable effective levels of attractancy to the flies. Acceptable levels of attractancy refers to the relative number of flies attracted to the attractant composition that attributes to the total or partial clearing of flies from a particular locale. An acceptable level of attractancy will vary based on the environment where the trap is positioned. For example, an acceptable level of attractancy in a livestock facility may be much different from an acceptable level of attractancy in a residence.

Adjuvants are known in the arts of insect attractants and room fresheners and include a variety of floral odors. Further, other agents can be added to augment the attractancy of the composition. Adjuvants and masks can be tested with the compositions of this invention using the wind tunnel testing regime as provided in Example 3 and as provided in the release and recapture studies of Examples 4–6.

In a preferred embodiment, the compositions of this invention are combined with an insect trap to catch insects attracted to the composition. The trap includes any of a variety of means for retaining the flies at or near the trap. Means for retaining flies include those known in the art such as adhesives, electrocution, toxicants, mazes (i.e., pitfalls), liquids to facilitate drowning, and/or insecticides. For example, the composition can be incorporated into a tacky or adhesive matrix and placed on a surface to trap the flies. Fly paper and tacky substances for trapping insects in pheromone traps and the like are known in the art. Preferably, the composition can be incorporated into a sustained release device and placed on or near a trap to retain the flies. Sustained release devices include dispensers that support release of the attractant compositions of this invention over time, preferably for more than about 72 hours and therefore maintains the ability of the device or dispenser to attract flies for about 72 hours. A variety of other fly traps and insect traps are known in the art including "bug zappers", trap boxes, including mazes, death traps, fly paper, traps using air to draw insects toward the source, traps that attract with UV light or electromagnetic fields, traps that electrocute, and the like, and those of ordinary skill in the art will be able to combine the compositions of this invention with insect traps and with composition release devices, such as sustained released dispensers, without undue experimentation.

Traps preferably include at least one attractant and at least one means for retaining the targeted insect. Trapping insects, and in particular flies, is important in livestock facilities where the population of flies, particularly during fly outbreaks, can be quite large. Similarly in the residential, health care and food-related commercial industries, trapping is important. The traps are preferably able to trap large numbers of flies for livestock applications and in other embodiments the traps are preferably pleasant in appearance for residential and some commercial applications. There are a variety of fly traps for residential use and the composition of this invention could be readily incorporated into these traps. Similarly, traps are known for use in areas where there are large outbreaks of flies. An example includes the fly traps available from, for example, the Farnam Companies, Inc. (Phoenix, Ariz.). These traps use a liquid attractant and the compositions of this invention could be incorporated into these traps formats without undue experimentation.

As illustrated in Example 6, a preferred format for residential, health care and food service related areas is provided in a sustained release format such as that of a pump (including an atomizer, an aerosol cannister delivering metered doses on a timed basis), a matrix or a membrane format that supports the volatiles for sustained release. Sustained release pumps, including atomizers and metered aerosols, and other sustained release dispensers are known in the art, and matrices, including gel matrices that support the sustained release of a composition either alone or in combination with a heat source are known. Other sustained release mechanisms would function in this invention where a small amount of the composition is released into the environment over an extended period. Advantageously, the sustained release format permits small amounts of the compositions of this invention to be released continuously over time at a level that is attractive to flies but is barely detectable or undetectable to the human nose. Alternatively, in combination with the sustained release format, adjuvants and masks, as discussed above, can be used in the sustained release formulations to conceal the odors associated with the attractants. Example 6 and Table 9 provide one format that optimizes insect attractancy while minimizing odor and provides a useful indoor commercial format.

For livestock applications or other areas where fly concentrations can be a problem, the importance of fly attraction is greater than the need to mask odors associated with the attractant. In these cases, greater concentrations of the attractants can be used, larger numbers of the attractant/trap units can be distributed in a given area, and the like, to ensure maximal fly trapping in the context of high aerial background concentrations of malodorous compounds.

In another embodiment of this invention, the compositions are used in combination with a toxicant, such as insecticide. Further, the compositions either alone or in combination with an insecticide can be used as a decoy to draw the flies to a desired sight, away from, for example, people, food, or livestock. The composition can be incorporated into any suitable support including a matrix, a wicking device or a sustained release dispenser.

Brown et al. 1961, Frishman & Matthysse 1966, Mulla et al. 1977 (all supra) have reported that house flies can be attracted to single odor sources including indole, 3-methylindole, or butanoic acid. The wind-tunnel behavioral assays did not show any significant attractancy for these or other individually tested organic volatiles from pig manure. Although this may be due to the concentration differences of the compounds employed in field trapping studies, high concentrations of any one compound that is malodorous to humans would be unsuitable for an indoor insect attractant.

Figure 2:
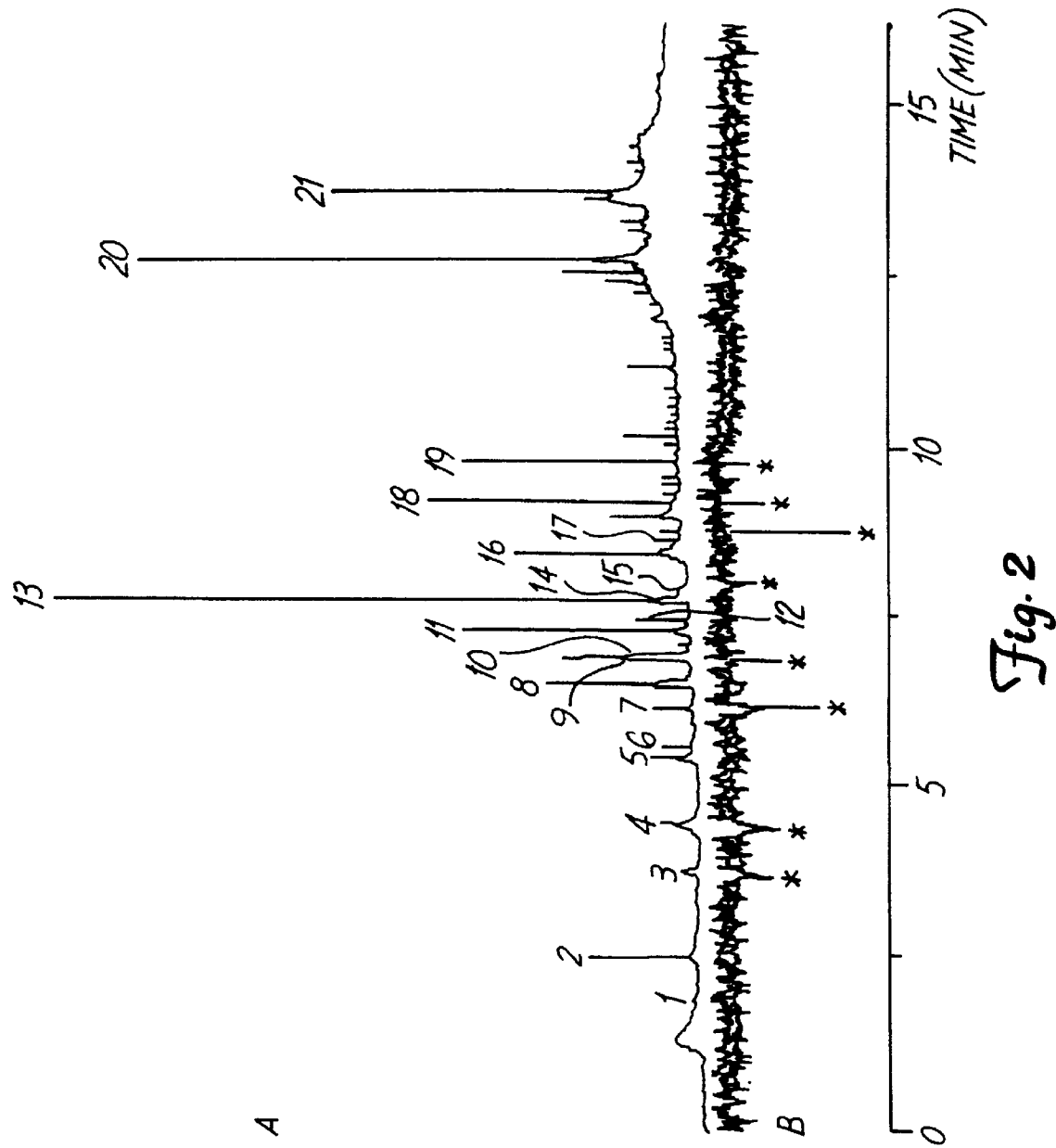
FIG. 2 is a simultaneously recorded gas chromatogram of pig manure volatiles collected by solid phase microextraction (A) and electroantennogram of a female house fly antenna (B). Based on the parameters of this study, electrophysiologically active compounds are labeled with an asterisk and number labels indicated identified materials in Table 1.

Several of the identified EAG-active compounds also have been found to evoke antennal responses in other Diptera. Tsetse flies (Glossina spp.) are attracted to buffalo and ox urine, and both EAG and single-cell recordings have shown that attractiveness of urine can be attributed to the presence of phenol, 3- and 4-methylphenol, 3- and 4-ethylphenol, as well as 4-n-propylphenol (Den Otter 1991, *Physiol. Entomol.* 16:401–410; Den Otter et al. 1993, *Physiol. Entomol.* 18:43–49; and, Saini & Hassanali 1992, *Insect Sci. Applic.* 13:95–104). EAG work performed using the stable fly, *Stomoxys calcitrans* (L.), demonstrated the electrophysiological activity of 3-methylphenol (Schofield et al. 1995, *Physiol. Entomol.* 20:273–280), but responses to butanoic acid as well as the earlier published EAG-active acetic acid (Warnes & Finlayson 1986, *Physiol. Entomol.* 11:469–473) were not significant. These phenolic compounds, with the exception of a 4-n-propylphenol, have been identified in swine waste (Spoelstra 1980, supra and O'Neill & Philips 1992, supra), and at least four of these compounds (phenol, 3- 4-methylphenol, and 4-ethylphenol) have been positively identified in our solid phase microextraction headspace sampling of pig manure. However, 4-methylphenol, one of the most important components in an attractant blend for Glossina species did not elicit any EAG response with female house fly antennae, even though it is the most abundant component in the pig manure (FIG. 2 and Table 1). Likewise, no significant EAG responses occurred when 3-methylphenol or 4-ethylphenol eluted from the GC column. The only phenolic compound that did elicit a significant response with female house fly antennae was phenol (Table 1). In dose-response series, EAGs from female house flies only started to increase at the 1 mg dosage level, suggesting that there are fewer receptors for phenolic compounds on the antennae of house flies than on stable fly and tsetse fly antennae.

Cork (1994, *Med. Vet. Entomol.* 8:151–159) identified several EAG-active compounds from larval wound fluid that elicited responses from screwworm, *Cochliomyia hominivorax* (Coquerel), antennae. The array of compounds identified from wounds was similar to that found in the headspace of our pig manure samples. Cork (supra) showed that relatively strong EAG responses were evoked with 1-octen-3-ol, 3-methylphenol, indole, phenol, dimethyldisulfide, and 3-methylindole, even though the latter was not present in larval wound fluid. Benzeneethanol present in the larval wound fluid was mentioned to be EAG active. Several of the volatile fatty acids tested with C. hominivorax also were present in the pig manure samples (Table 2), but only butanoic acid and 3-methylbutanoic acid elicited a response from female house fly antennae.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully practice and obtain the compositions of the intended invention.

EXAMPLE 1

Collection of Pig Manure Volatiles

Pig manure, comprised of pig urine and feces, was gathered immediately after excretion. The manure was divided into 2.5-g samples that were placed in 2-dram (7.4-ml) vials filled with 2.5 g of HPLC-grade water and capped with Teflon-coated septa (Supelco, Inc., Bellefonte, Pa.). Fifty-gram samples also were prepared and placed in 100-ml polypropylene bottles filled with 50 g of HPLC-grade water. All samples were stored at −20° C.

Headspace collection of volatiles from the pig manure were obtained by two different methods. The first method, which does not require the use of solvents, collected pig manure volatiles directly from 2-dram sample vials by solid phase microextraction (SPME) (Supelco, Inc., Bellefonte, Pa.). The SPME unit consisted of a fiber coated with 100 $\mu$m of polydimethylsiloxane contained within a syringe. The fiber was extruded from the syringe and inserted into the headspace of a 2-dram vial containing pig manure for 10 min at room temperature (ca. 25° C.–28° C.), after which it was retracted and immediately inserted into the injector port of a GC (HP 5890 gas chromatograph, Hewlett-Packard Co., Palo Alto, Calif.) where it was thermally desorbed. For the second method, a 50-g pig manure sample was placed in a two-necked 250-ml flask. Charcoal-filtered air was blown over magnetically stirred manure at a rate of 3 ml/s for 16 h at room temperature. Volatiles were collected in a glass tube (10 cm long×4 mm interior diameter [RD]) containing 50 mg of pre-cleaned Tenax® TA (Alltach Associated, Inc., Deerfield, Ill.) placed between two glass wool plugs. The Tenax® TA trap was desorbed with 1 ml of redistilled HPLC-grade hexane. Each sample was concentrated to ca. 200 $\mu$l under nitrogen and immediately analyzed by GC-EAG and GC-MS.

Chemical analysis. One-microliter aliquots of the Tenax® TA-collected pig manure volatiles were injected in spitless mode onto 30 m×0.25 mm ID fused silica capillary gas chromatographic columns, coated either with DB-1 or DB-225 (J & W Scientific, Folson, Calif.) for analysis by GC-EAG and GC-MS. Column conditions were as follows: He carrier gas flow of 1.5 ml/min, injector temperature 250° C., 1 min delay on inlet purge, 4 min at 35° C. then 25° C./min to 320° C. (DB-1) or 15° C./min to 220° C. (DB-225). The SPME samples were analyzed by using the above mentioned conditions with a 4-min delay on inlet purge.

GC-MS analyses were performed by using the HP 5890 GC with a direct interface to a Hewlett-Packard 5970 mass selective detector (electron impact, 70 eV).

Analyses of pig manure volatiles. Twenty-two GC-EAG analyses of the volatiles collected form pig manure were obtained by using 22 different female house fly antennae. Only those GC peaks that consistently revealed simultaneous EAG activity were targeted for further analysis although similar analyses could be performed on compounds stimulating any EAG activity. GC-EAG analyses consistently revealed eight GC peaks on both DB-1 and DB-225 columns with corresponding EAG activity on female house fly antennae (FIG. 2 and Table 1, peak nos. 3, 4, 7, 9, 15, 17, 18, and 19). The retention times on both columns and GC-MS spectra of peak no. 3, 4, 7, 9, 15, 17, 18, and 19 corresponded precisely to those of eight compounds known to be present in the headspace of pig manure: butanoic acid, 3-methylbutanoic acid, dimethyltrisulfide, phenol, benzeneethanol, dimethyltetrasulfide, indole, and 3-methylindole, respectively. Moreover, combined GC-EAG recordings on both DB-1 and DB-225 columns demonstrated that butanoic acid, 3-methylbutanoic acid, dimethyltrisulfide, phenol, benzeneethanol, dimethyltetrasulfide, indole, and 3-methylindole had retention times identical to peak no. 3, 4, 7, 9, 15, 17, 18, and 19, respectively, from the collected pig manure volatiles, and that these compounds were EAG-active (Table 1). Seven of our 22 GC-EAG analyses showed an additional (ninth) EAG-active peak, and a subsequent GC-MS library search tentatively identified this peak as dimethyldisulfide (Table 1). Comparison between SPME-collected volatiles vs. Tenax® TA-collected materials revealed no prominent differences in the number of compounds detected. However, there were differences in the ratios of the compounds collected via each method, and compounds eluding from the capillary columns during the first 3 min of the runs where hidden by the solvent peak in the Tenax® collection method. In both methods, 4-methylphenol was the major compound collected.

EXAMPLE 2

Electroantennogram Analysis of Pig Manure Volatiles

Musca domestica were obtained as pupae from a colony maintained at the Department of Entomology, Iowa State University, and kept at 25° C. under a 14:10 (light:dark) h photoperiod regime until they emerged. Adults were chilled (ca. 90 s at −20° C. and the sexes separated within 12 h after they emerged. Males and females were placed in separate cages and given access to water and a mixture of dry whole milk and powdered sugar (1:1). Flies used in experiments were between about 5 and 16 d old. The flies were used for antennae isolation as described below or in flight direction testing as provided in Example 3.

Electroantennogram responses. Simultaneous GC-EAG and EAG analyses were performed according to standard methods (e.g. Cossé et al. 1994, J. Chem. Ecol. 21:1823–1836 and Baker et al. 1991, J. Chem. Ecol. 17:1973–1988) by using a HP 5890 GC. EAG recordings were made by inserting a glass pipette Ag/AgCl saline electrode (World Precision Instruments, Sarasota, Fla.) in the back of an excised house fly head. A second saline recording electrode was placed in contact with the distal end of the funiculus of one of the antenna. Both pipettes were filled with Beadle-Ephrussi (Ephrussi & Beadle. 1936, Am. Nat. 70:218–225) saline. To examine antennal sensitivity to the identified pig manure volatiles, EAGs that were not coupled to the GC were recorded in response to a dose-response series of commercial compounds. Serial dilutions of the tested compounds were made in redistilled HPLC-grade methylene chloride such that the tested compounds were applied to filter-paper-strips (0.5 cm×3.0 cm, Whatman No. 1) in 10 $\mu$m of solvent. The filter-paper-strips were placed inside glass Pasteur pipettes (15 cm long). The antenna was continuously flushed with a charcoal-filtered and moistened airstream. The air, flowing at a rate of 20 ml/s, was delivered through a glass tube (8 mm ID) ending 10 mm in front of the preparation. Two milliliters of the atmosphere of the stimulus pipette was puffed into the constant airstream by a mechanical puffing device (Synteck, Hilversum, The Netherlands), delivering 0.1-s puffs. The stimulus was injected into the airstream 15 cm upstream from the antenna. Control puffs (filter paper plus solvent) were presented to each EAG preparation before and after the test compounds. To compensate for possible deterioration of the preparation and differences in quality of the electrical connection, EAG amplitudes were normalized by dividing the amplitude of the EAG generated from a test compound by the mean of the control response. Each value thus yielded an estimate of relative EAG amplitude. Within a particular series of test compounds, presentation of the test compounds was randomized. EAG data were subjected to ANOVA and mean responses were compared by using the LSD method (Sokal & Rohlf 1981. *Biometry*. W. H. Freeman & Company, San Francisco, 859 pp.).

The EAG responses of female house fly antennae to puffs of seven of the GC-EAG-active compounds were recorded at five dosages. EAG amplitudes increased to puffs from cartridges containing from 0.1 µg up to 100 µg for all of the compounds tested. All responses were significantly higher than those from the control (solvent) cartridges. Even at the lowest dosage tested, the responses to all of the compounds were at least 1.5-times greater than to those of the control. Analysis of variance of the antennal responses indicated that there were significant differences not only between the responses of the flies to the various doses tested ($F=227.34$, $df=4, 315$; $P<<0.001$) and between the different chemicals ($F=73.76$, $df=6, 315$; $P<<0.001$) but also that the interaction between doses and chemicals was significant ($F=21.96$, $df=25, 315$; $P<<0.00 1$). Furthermore, the data show that, of the compounds tested, butanoic acid elicited the highest EAG responses at all dosages except 0.1 µg. Conversely, benzeneethanol elicited the lowest responses at all dosages except 0.1 µg. The EAG responses elicited by 3-methylindole and indole were not significantly different from each other at all dosages tested. The dose-response curves also indicate that maximum responses had been reached at the 100-µg dosage with butanoic acid, 3-methylbutanoic acid, 3-methylindole, and dimethyltrisulfide, whereas responses to the 1,000-µg dosage of indole, phenol, and benzeneethanol had still not peaked.

The solid phase microextraction (SPME) headspace sampling with GC separation provided a useful method for analyzing volatiles emitted by pig manure. The use of this technique overcomes many of the drawbacks that can occur with more standard methods, and all of the GC-EAG spectra we obtained exhibited a high degree of uniformity.

TABLE 1

Analytical results of pig manure volatiles.

| Peak no.[a] | Compound | GC-EAG active[b] | Identification[c] |
|---|---|---|---|
| 1 | dimethyldisulfide | + | MS |
| 2 | acetic acid | − | MS |
| 3 | butanoic acid | + | GC & MS |
| 4 | 3-methylbutanoic acid | + | GC & MS |
| 5 | pentanoic acid | − | MS |
| 6 | hexanoic acid | − | MS |
| 7 | dimethyltrisulfide | + | GC & MS |
| 8 | α-pinene | − | GC & MS |
| 9 | phenol | + | GC & MS |
| 10 | β-pinene | − | GC & MS |
| 11 | δ-3-carene | − | GC & Ms |
| 12 | limonene | − | MS |
| 13 | 4-methylphenol | − | GC & MS |
| 14 | 3-methylphenol | − | GC & MS |
| 15 | benzeneethanol | + | GC & MS |
| 16 | 4-ethylphenol | − | GC & MS |

TABLE 1-continued

Analytical results of pig manure volatiles.

| Peak no.[a] | Compound | GC-EAG active[b] | Identification[c] |
|---|---|---|---|
| 17 | dimethyltetrasulfide | + | GC & MS |
| 18 | indole | + | GC & MS |
| 19 | 3-methylindole | + | GC & MS |
| 20 | hexadecanoic acid | − | MS |
| 21 | octadecanoic acid | − | MS |

[a]Numbers correspond to labeled peaks in FIG. 1.
[b]Gas chromatographic-coupled-electroantennogram (GC-EAG) (see also FIG. 1); +, active; −, not active.
[c]Identification is based on a mass spectrum library search (MS) and/or comparison of mass spectra of the natural material with that of the identified synthetic compound (GC-MS).

EXAMPLE 3

Wind Tunnel Behavioral Bioassays

The following chemicals were used in the wind tunnel and free room attractant testing: Butanoic acid, 3-methylbutanoic acid, 3-methylindole, indole, 3-methylphenol, 4-methylphenol, and benzeneethanol were obtained from Sigma Chemical Co. (St. Louis, Mo.) and were >99% pure (label information and GC analyses). Phenol, δ-3-carene, (±)-α-pinene, (IS)-(−)-β- pinene, and 4-ethylphenol were purchased from Aldrich Chemical Co. (Milwaukee, Wis.) and were >99% pure. Dimethyltrisulfide was obtained from Narchem Corp. (Chicago, Ill.) and was >99% pure. The dimethyltetrasulfide, purchased from Oxford Organics, Inc. (Elizabeth, N.J.) was a mixture of dimethyltetrasulfide (33%) and dimethyltrisulfide (50%) based on GC-MS comparisons with the commercial sample of dimethyltrisulfide.

Wind tunnel. Behavioral assays were conducted in a modified 2.4 m×1.0 m×1.0 m wind tunnel described previously by Miller & Roelofs (1978. *J. Chem. Ecol.* 4:187–198). The wind speed was adjustable (0 to 100 cm/s) and was set at 50 cm/s. The temperature in the wind tunnel was about 23 ±2° C. White paper covered the outside of the tunnel to eliminate potential distractions to flies and diffused the light coming from four pairs of white fluorescent lamps running the length of the tunnel top and positioned I m above the ceiling of the tunnel. A visual pattern consisting of 6-cm-diam red vinyl dots was placed underneath the transparent tunnel floor. Small flaps covering peep holes in the white-paper paneling were opened from time to time to allow for observations of the flies during experiments. The flight tracks of the flies, together with the audio observations of the experimenter, were recorded onto cassette tape by using a Toshiba KV 6300A recorder and a Sony M374 black-and-white video camera located ca. 50 cm above the ceiling of the tunnel. The field of view for all recordings was 1.2 m long extending from 55 cm to 175 cm downwind from the upwind end of the tunnel and extending the width of the tunnel. Recordings of fly behaviors were played back in slow motion through a 47.5-cm black-and-white Panasonic WV 5470 television monitor.

Wind-tunnel behavioral bioassays. Virgin females were placed in groups of five or six in screened release cages (6 cm×10 cm ID), covered with Petri dish lids, 3 h before being tested, and then were released between 5–8 h into the photophase. The release cage was placed on a platform (15 cm×15 cm) 60 cm away from the downwind screen and 25 cm above the tunnel floor. The Petri dish lid was attached to a wire that was pulled up from the tunnel top ca. 15 s after the introduction of the odor source. The clear Petri dish lid together with its friction-free rapid removal prevented the evocation of an escape response in the files (Holmqvist & Srinivasan 1991, *J. Comp. Physiol.* A 16:451–459). The odor source, formulated in 10 ml of water, was introduced in a Petri dish (1.5 cm×10 cm ID) placed on a platform 60 cm away from the upwind screen and 25 cm above the tunnel floor. The odor source was presented as a turbulent plume (as visualized by $TiCl_4$ smoke prior to the bioassays) that moved over and through the release cage. The distance between the release cage and odor source was 1 m. In addition to video recording, the behavior of flies was recorded by the experimenter from the side, who observed whether or not the flies were flying at the height of the odor plume and also gave additional information about the 3-dimensional aspects of the flight tracks. Tracks were recorded for 4 min after the removal of the Petri dish cover. Upon analysis during replay those tracks in which flies exhibited plume-oriented upwind flight behavior were scored for the upwind flight distance attained by the flies (either 60 cm or 95–100 cm from the release point) and also for whether or not the flies landed on the source. The upwind progress score was calculated per fly unit, with a fly unit expressed as the total number of plume-oriented upwind flights per group divided by the number of individual flies per group. Odor sources were chosen at random, each source was tested on one single day, and the experiments were performed for 12 consecutive days. The data were subjected to ANOVA and means were compared by using the T-method (Sokal & Rolhf 198 1, supra).

Flight track analyses. Individually released females had their upwind flight tracks video-recorded from ca. 50 cm above the tunnel ceiling by using two Sony M374 black-and-white video cameras connected to two Toshiba KV 6300A video recorders. Measuring the total field of view of the partial overlapping camera views at the level of a $TiCl_4$ smoke plume (25 cm above the wind tunnel floor) yielded a 1.0 m (1.4 m rectangular area, which extended from 40 cm to 180 cm downwind from the upwind end of the tunnel. Only flight tracks of females that flew upwind in the plume and contacted the pig manure (2.5 g in 10 ml of $H_2O$) odor source were analyzed. The recordings of the female flight tracks were played back frame-by-frame through a 47.5-cm black-and-white Panasonic WV 5470 television monitor. Every other frame (each $\frac{1}{30}$th s) together with three points of reference on the wind tunnel floor and the fly's location were captured by using a computer video frame-grabber board (Odavision4, Hammerkop Co., Mass.). The X and Y coordinates of the fly location in a two-dimensional plane were obtained by using digitizing Mantid computer software (Hammerkop Co., Mass.) and were analyzed for net upwind flight speed. The release of the individual females was similar to that described for the wind-tunnel bioassays with the exception that the release cage and odor source were placed 50 cm away from the tunnel ends, creating a distance of 1.2 m between release cage and odor source.

Figure 3:
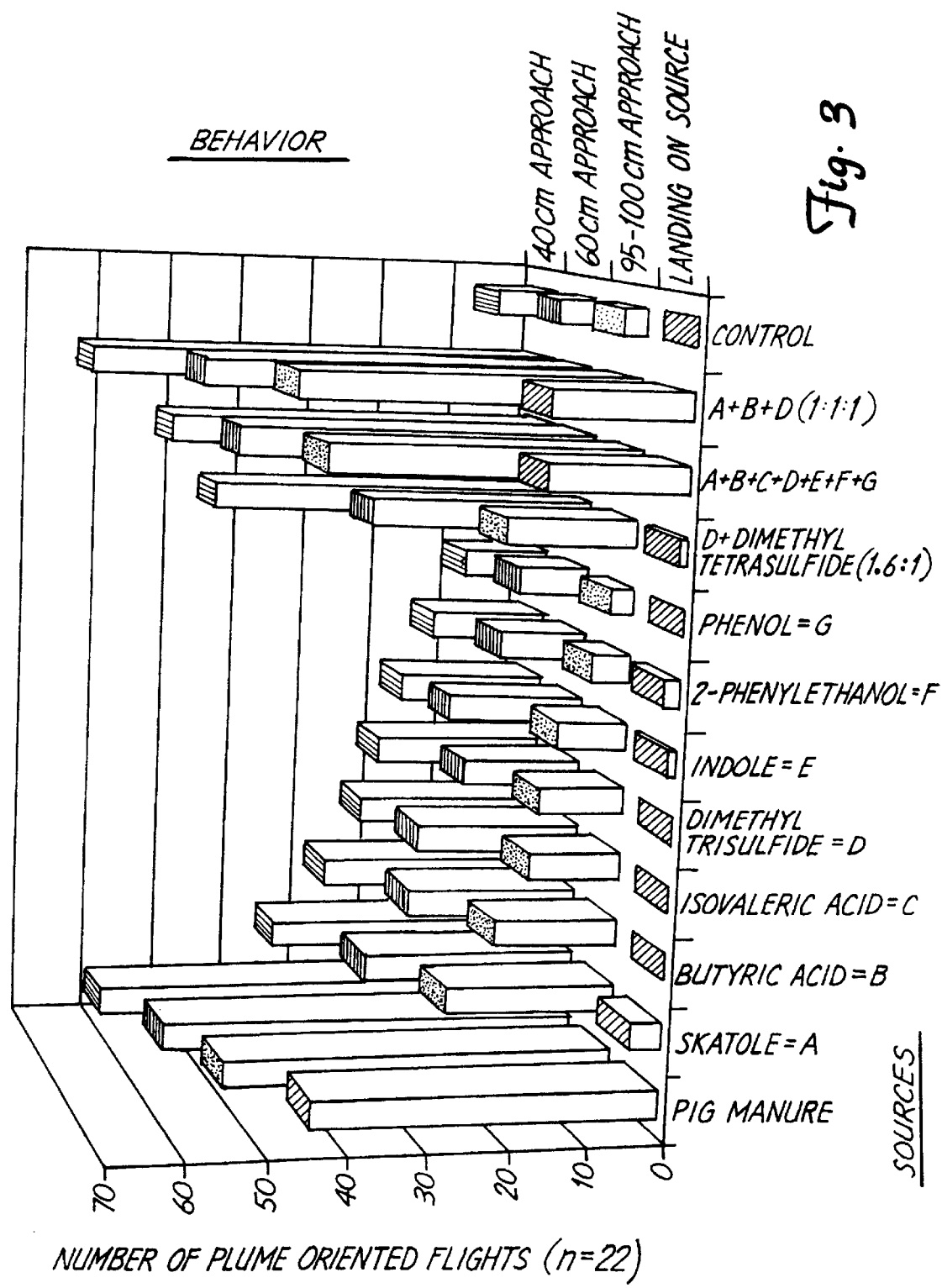
FIG. 3 is a graphic display summarizing female house fly wind tunnel behavioral responses to pig manure volatiles, synthetic pig manure volatiles and mixtures of synthetic pig manure volatiles. Odor sources were formulated in 10 ml of water at dosages of 20 µg except for pig manure (2.5 g).
Figure 4:
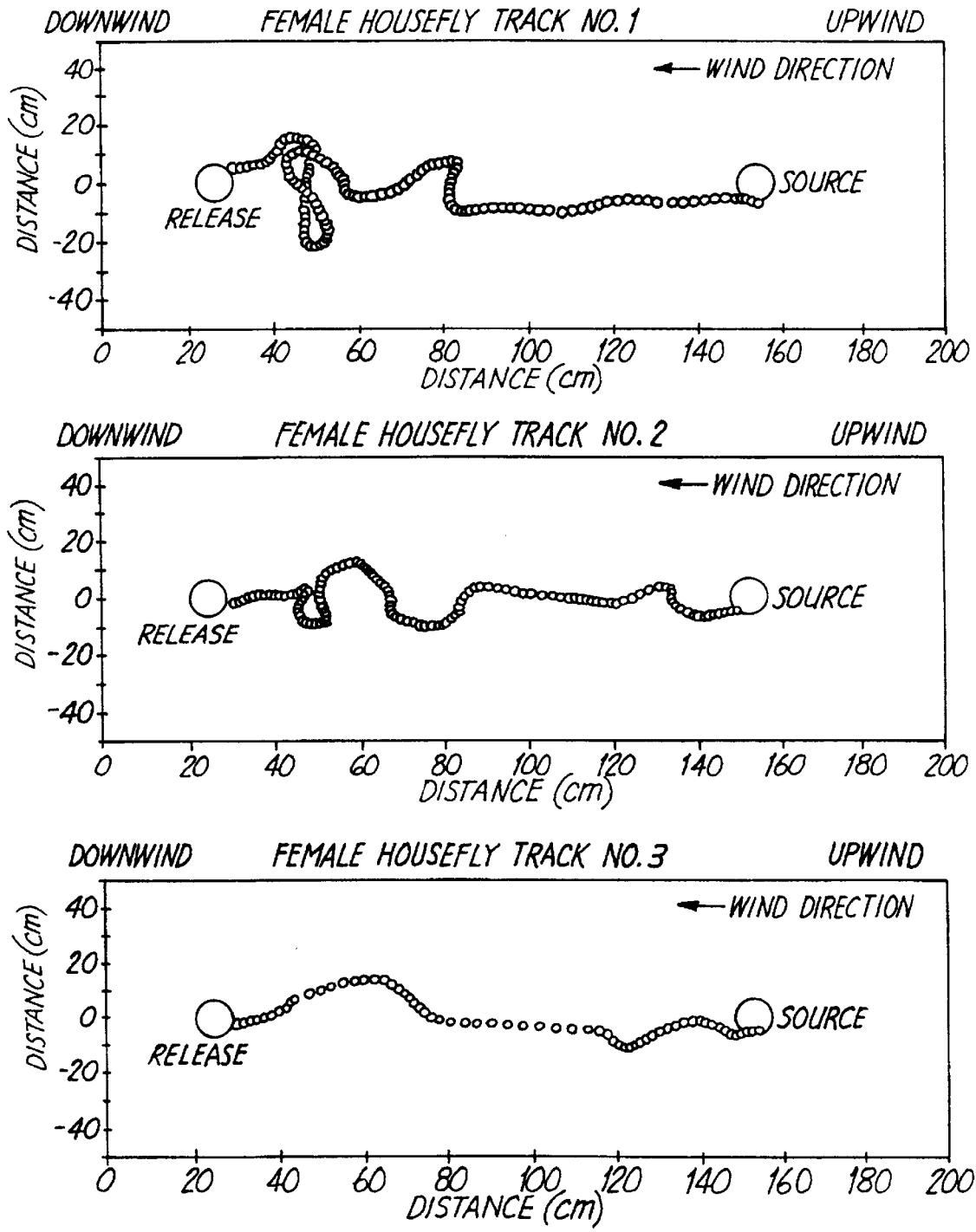
FIG. 4 provides three flight tracks of flying M. domestica females in response to pig manure odor (2.5 g in 10 ml of water). Large rectangular boxes represent the wind-tunnel floor area. Wind speed was set at 50 cm/second. Dots are 1/30 th of a second (s) apart.

Virgin female house flies readily flew upwind to volatiles emitted from pig manure: 44 landings on the source were recorded using four groups of flies (totaling 22 flies released) (FIG. 3). Female flies also flew upwind and landed on the source in response to volatiles emitted from mixtures of chemicals identified from the headspace of pig manure. In instances where extended observations of individual flies were possible, flies made several upwind-oriented flights in the plume of varying distances and made several successful landings on the source during the 4-min response time. Typically, after removal of the Petri dish cover, the quiescent female would remain inactive for several seconds before flying upwind in a zigzag pattern toward the pig manure source. Females that upon release flew upwind in the plume and landed directly on the source exhibited a mean net upwind flight speed of 40.4 cm/s (±14.4 SD, n=4) (FIG. 4). Of the females released in groups of five or six, only a few flew directly to the manure, the majority flying toward the source in the plume and aborting their upwind progress at various distances downwind of the source. Those females that landed on the source were observed to feed. Analysis of variance of the behavioral responses showed that there were significantly more upwind flights and landings on the source with pig manure than with the water control (Table 2). The attractancy of individual EAG-active compounds was not significantly different than that of the control. However, two mixtures, one composed of seven EAG-active compounds and a second made up of equal amounts of butanoic acid, 3-methylindole, and dimethyltrisulfide, elicited upwind flights at a rate not significantly different than that to pig manure. However, the rate of landing on the source was lower than that evoked by pig manure. The frequencies of upwind flight and landing on the source in response to these synthetic mixtures were, however, significantly higher than that of the control.

TABLE 2

Wind tunnel behavioral responses of house flies to pig manure, individual pig manure volatiles, and mixtures of pig manure volatiles.

| | | Plume-oriented upwind progress/fly unit[a] | | | | | |
|---|---|---|---|---|---|---|---|
| | | 60 cm | | 95–100 cm | | landing on source | |
| Source[b] | Groups[c] | mean | ± SD[d] | mean | ± SD[d] | mean | ± SD[d] |
| pig manure | 4 | 2.50 | ± 0.69a | 2.33 | ± 0.48a | 2.01 | ± 0.55a |
| 3-methylindole (I) | 4 | 1.23 | ± 0.91ab | 0.98 | ± 0.62bcd | 0.18 | ± 0.14c |
| butanoic acid (II) | 4 | 1.00 | ± 0.32ab | 0.74 | ± 0.29bcd | 0c | |
| 3-methylbutanoic acid (III) | 4 | 0.88 | ± 0.94ab | 0.51 | ± 0.48bcd | 0c | |
| dimethyltrisulfide (IV) | 4 | 0.68 | ± 0.34ab | 0.48 | ± 0.23bcd | 0c | |
| indole (V) | 4 | 0.76 | ± 0.38ab | 0.41 | ± 0.26cd | 0.04 | ± 0.08c |
| benzeneethanol (VI) | 4 | 0.53 | ± 0.32b | 0.24 | ± 0.25d | 0.09 | ± 0.11c |

TABLE 2-continued

Wind tunnel behavioral responses of house flies to pig manure, individual pig manure volatiles, and mixtures of pig manure volatiles.

| | | Plume-oriented upwind progress/fly unit[a] | | | | | |
|---|---|---|---|---|---|---|---|
| | | 60 cm | | 95–100 cm | | landing on source | |
| Source[b] | Groups[c] | mean ± SD[d] | | mean ± SD[d] | | mean ± SD[d] | |
| phenol (VII) | 4 | 0.44 | ± 0.53b | 0.15 | ± 0.30d | 0c | |
| IV + dimethyltetrasulfide (1.5:1)[f] | 4 | 1.38 | ± 0.90ab | 0.80 | ± 0.38bcd | 0.04 | ± 0.08c |
| I + II + IV (1:1:1) | 4 | 2.34 | ± 1.40a | 1.97 | ± 1.14ab | 0.80 | ± 0.42b |
| I + II + III + IV + V + VI + VII (1:1:1:1:1:1:1) | 4 | 2.12 | ± 1.42ab | 1.78 | ± 1.27abc | 0.81 | ± 0.55b |
| control (10 ml of H$_2$O) | 4 | 0.24 | ± 0.25b | 0.15 | ± 0.19d | 0c | | a Fly unit is expressed as the total number of plume-oriented flights per group divided by the number of individual flies per group.
b 20 µg suspended in 10 ml of H$_2$O.
c Four groups of 5 or 6 females each, totaling 22 females.
d Means in the same column having at least one letter in common are not significantly different by the T-method (Sokal & Rohlf 1981) at $P < 0.05$.
e 2.5 g suspended in H$_2$O.
f 120 pg in total.

EXAMPLE 4

Testing to Optimize Attractant Compositions

Various combinations of volatiles identified from FIG. 3 were tested in wind tunnel trapping and compared to control samples. The control is a similar filter paper to which was applied 30 µl of methylene chloride which was used as a solvent of the synthetic compounds. In one study, 30 mated females were released in a laboratory and the number of flies trapped on tacky cardboard strips during the first twenty minutes after release were counted. Experiments were performed in triplicate. The pig manure volatiles were applied on filter paper disks and a 2% solution of (NH$_4$)$_2$CO$_3$ was placed in an inverted one dram vial with a cotton dental roll. Both release devices were placed behind a strip of white vertical sticky cardboard that was used as a trap. Although 30 mated female flies/replicate (a total of 90 flies per each treatment) were used in this study, studies performed as part of this invention, male flies responded similarly. The control used in these studies was filter paper with methylene chloride solvent.

TABLE 3

Wind tunnel trapping of female house flies[1] with pig manure volatiles[2]

| Treatment[3] | n | mean trapped[4] |
|---|---|---|
| BA + DMTS + 3MIN | 3 | 10.33 |
| BA + DMTS + IN | 3 | 10.33 |
| BA + DMTS + Ph | 3 | 6.67 |
| BA + DMTS + 3MBA | 3 | 6.00 |
| BA + DMTS + BENZ | 3 | 3.33 |
| Control | 3 | 3.67 |

[1] released 30 mated females/replicate
[2] BA '2 Butanoic acid, DMTS = Dimethyltrisulfide, 3MIN = 3-Methylindole, IN = Indole, Ph = Phenol, 3MBA '2 3-Methyl butanoic acid, BENZ = Benzeneethanol
[3] 20 µg of each compound applied on filter paper disk
[4] mean number of flies trapped on white sticky cardboard strips during the first 20 min after release

EXAMPLE 5

Fly Attractant Compositions Comprising (NH$_4$)$_2$CO$_3$

In another set of experiments a combination of compounds and single compounds (Tables 4 through 6) were tested in combination with (NH$_4$)$_2$CO$_3$. Initial studies were performed in wind tunnel trapping experiments. Equal volumes of each compound to be tested were applied alone or in combination on a filter paper disk with a 2% solution of (NH$_4$)$_2$CO$_3$ presented in a 1 dram vial with a dental roll. As described for Table 3, the mean number of flies trapped on white sticky cardboard strips was calculated after the twenty minutes. Results from these experiments demonstrated that: 1) ammonia with the pig manure volatiles mixture was a better attractant than ammonia alone (Table 4); 2) a composition with three components and ammonia was better than a combination of one with two compounds (Table 5); and, 3) individual compounds with ammonia could attract flies, but a composition with three components and ammonia showed the highest attractant activity.

TABLE 4

Wind tunnel trapping of female house flies[1] with pig manure volatiles[2] and ammonia

| Treatment[3] | n | mean trapped[4] |
|---|---|---|
| (NH$_4$)$_2$CO$_3$ (2% solution) | 3 | 10.00 |
| (NH$_4$)$_2$CO$_3$ + BA/DMTS/IN | 3 | 19.33 |
| Control | 3 | 2.67 |

[1] released 30 mated females/replicate
[2] BA '2 Butanoic acid, DMTS = Dimethyltrisulfide, IN = Indole
[3] 20 µg of each compound applied on filter paper disk, 2% (NH$_4$)$_2$CO$_3$ presented in 1 dram vial with dental roll
[4] mean number of flies trapped on white sticky cardboard strips during the first 20 min after release

TABLE 5

Wind tunnel trapping of female house flies[1] with binary mixtures of pig manure volatiles[2] and ammonia

| Treatment[3] | n | mean trapped[4] |
|---|---|---|
| $(NH_4)_2CO_3$ + BA/DMTS/IN | 5 | 18.40 |
| $(NH_4)_2CO_3$ + BA/IN | 5 | 14.40 |
| $(NH_4)_2CO_3$ | 5 | 10.20 |
| $(NH_4)_2CO_3$ + DMTS/IN | 5 | 10.20 |
| $(NH_4)_2CO_3$ + BA/DMTS | 5 | 15.20 |
| Control | 5 | 4.20 |

[1] released 30 mated females/replicate
[2] BA '2 Butanoic acid, DMTS = Dimethyltrisulfide, IN = Indole
[3] 20 μg of each compound applied on filter paper disk, 2% $(NH_4)_2CO_3$ presented in 1 dram vial with dental roll
[4] mean number of flies trapped on white sticky cardboard strips during the first 20 min after release

TABLE 6

Wind tunnel trapping of female house flies[1] with single pig manure volatiles[2] and ammonia

| Treatment[3] | n | mean trapped[4] |
|---|---|---|
| $(NH_4)_2CO_3$ + BA/DMTS/IN | 6 | 18.50 |
| $(NH_4)_2CO_3$ + BA | 6 | 14.30 |
| $(NH_4)_2CO_3$ + DMTS | 6 | 12.20 |
| $(NH_4)_2CO_3$ + IN | 6 | 13.50 |
| $(NH_4)_2CO_3$ | 6 | 10.20 |
| Control | 6 | 3.00 |

[1] released 30 mated females/replicate
[2] BA '2 Butanoic acid, DMTS = Dimethyltrisulfide, IN = Indole
[3] 20 μg of each compound applied on filter paper disk, 2% $(NH_4)_2CO_3$ presented in 1 dram vial with dental roll
[4] mean number of flies trapped on white sticky cardboard strips during the first 20 min after release In all of these tests the pig manure volatiles were applied on filter paper disks and the 2% solution of $(NH_4)_2CO_3$ was placed in an inverted one dram vial with a cotton dental roll. Both release devices were placed behind a strip of white vertical sticky cardboard that was used as the trap.

In Table 7, the attractants of this invention were combined in a 2% solution of $(NH_4)_2CO_3$. Here, two commercial fly traps (Eaton's Answer Fly-glue-Trap without the sugar coated fly pheromone crystals) was placed in a lab room with an undetermined number of free flying flies. The control contained a vial filled with water and a dental roll, while the test samples were vials filled with the test compounds in a 2% w/v $(NH_4)_2CO_3$ solution (in water) and a dental role. In four separate experiments, lasting about 24 hours each, the baited traps caught far more flies than the control. Most of the flies were caught in the first few hours, indicating that the bait quickly lost its attractivity due to the choice of release device (here the dental roll) and the high volatility of the compounds, that is, flies were still present but not attracted. The sustained release compositions as provided in one example in Example 6 address this problem. Furthermore, freshly prepared vials emitted a faint odor delectable to the human nose at a short distance (10–20 cm) from the vials.

TABLE 7

Trapping of free flying house flies[1] using Eaton's Answer Fly-glue-Traps

| | Trapped flies/24 h | |
|---|---|---|
| | Baited[2] | Control[3] |
| test 1 | 34 | 0 |
| test 2 | 35 | 1 |
| test 3 | 61 | 1 |
| test 4 | 66 | 6 |

[1] undetermined number of male and female present in the room
[2] 20 μg of Butanoic acid, Dimethylsulfide, Indole in 4.5 ml 2% $(NH_4)_2CO_3$ presented in 1 dram vial with dental roll
[3] 4.5 ml water in dram vial with dental roll A similar experiment was performed in a domestic environment (a home kitchen) as provided in Table 8 below. Table 8 details the results of the compositions of this invention in Eaton fly traps with and without the tertiary blend with and without ammonia. Pm and Pm[2] refer to two different sets of experiments. Pm refers to experiments that compared volatiles with ammonia as compared to an unbaited trap (Pm vs. Control) and Pm[2] compared volatiles with ammonia against a trap baited with fly pheromone (Pm2 vs. Ph). Results indicated that 70% of the released flies were recaptured within 6 hours, that the pig manure volatile composition was a better attractant than current fly pheromone bait on the market and that the laboratory results could be duplicated in a domestic environment.

TABLE 8

Release[1] and recapture of house flies in a domestic environment using Eaton's Answer Fly-glue-Traps

| | | mean trapped | | |
|---|---|---|---|---|
| Treatment | n | after 2 h | after 6 h | after 24 h |
| Pm[2] | 3 | 22 | 36.3 | 39 |
| Control[3] | 3 | 0.7 | 0.7 | 1.3 |
| Pm | 4 | 7.3 | 21 | 24 |
| Ph[4] | 4 | 3.8 | 8.5 | 9.5 |

[1] released 50 flies (male & female), 5–10 days old, fed 0.5 h prior to release
[2] 20 μg of Butanoic acid, Dimethyltrisulfide, Indole in 4.5 ml 2% $(H_4)_2CO_3$ presented in 1 dram vial with dental roll
[3] 4.5 ml of water in 1 dram vial with dental roll
[4] sugar coated fly pheromone crystals, supplied as bait for the Eaton's Answer Fly-glue-Traps (Sex-A-Trax)

EXAMPLE 6

Sustained Release Attractant Compositions

To overcome problems in delivering the compositions of this invention in a commercially useful form, we tested a timed pump sprayer (Virtual Aire, Waterbury Comp.) that can spray 70 μl/spray/5min. The pump contained a 200 ml water solution containing 2 g ammonium carbonate and about 1.4 mg each of the three compounds identified in the pig manure volatiles. This device permitted lower concentrations of compounds (0.5 μg/spray) at undetectable levels to the human nose up to 1 cm away, while keeping the release rate constant. The 300 ml bottle permitted at least 350 hrs of constant operation. The device was tested in a home setting to determine whether the results could be duplicated outside of the laboratory. Results using a timed pump spray are provided in Table 7. Using a low dosage at a constant release rate, the results indicated that on average, 65% of the flies were captured within 5 hours.

TABLE 9

Release[1] and recapture of house flies in a domestic environment using a timed spray machine[2]

| Treatment | n | mean trapped after 1 h | after 5 h | after 24 h |
|---|---|---|---|---|
| Pm[3] | 5 | 13.6 | 32.6 | 36.8 |
| Control[4] | 5 | 1.6 | 2.6 | 3.2 |

[1]released 50 flies (male & female), 5–10 days old, fed 0.5 h prior to release
[2]Virtual Aire pump sprayer, spraying 70 μl/spray/5 min onto filter paper placed directly behind a white sticky cardboard trap
[3]0.5 μg/spray of Butanoic acid, Dimethyltrisulfide, Indole in 2% $(NH_4)_2CO_3$
[4]unbaited white sticky cardboard trap It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A synthetic fly attractant composition comprising an effective amount of at least one ammonia-releasing compound, at least one volatile short chain carboxylic acid, at least one organic sulfide, and at least one nitrogen heterocycle.

2. The composition of claim 1 wherein the ammonia-releasing compound is selected from the group consisting of ammonium carbonate, ammonium chloride, ammonia gas and ammonium sulfate.

3. The composition of claim 1 wherein the volatile short chain carboxylic acid is selected from the group consisting of volatile short chain carboxylic acids that are naturally found in pig or cow manure.

4. The composition of claim 1 wherein the volatile short chain carboxylic acid is selected from the group consisting of straight or methyl-branched aliphatic carboxylic acids containing 2–5 carbon atoms.

5. The composition of claim 3 wherein the volatile short chain carboxylic acid is selected from the group consisting of butanoic acid and 3-methyl butanoic acid.

6. The composition of claim 1 wherein the organic sulfide is selected from the group consisting of organic sulfides that are naturally found in pig or cow manure.

7. The composition of claim 5 wherein the organic sulfide is selected from the group consisting of dimethyl disulfide, dimethyl trisulfide and dimethyl tetrasuflide.

8. The composition of claim 1 wherein the nitrogen heterocycles containing compound is selected from the group consisting of nitrogen heterocycles containing compounds that are naturally found in pig or cow manure.

9. The composition of claim 7 wherein the nitrogen heterocycles containing compound is selected from the group consisting of indole and 3-methyl indole.

10. The composition of claim 1 further comprising at least one additional component selected from the group consisting of volatile aromatic-containing alcohols and volatile amines that are naturally found in pig or cow manure.

11. The composition of claim 10 wherein the at least one additional component is selected from the group consisting of phenol, benzeneethanol, and trimethylamine.

12. The composition of claim 1 additionally comprising an insecticide.

13. The composition of claim 1 in a sustained release dispenser.

14. The composition of claim 13, wherein the pump includes an atomizer or a metered aerosol canister.

15. The composition of claim 14 wherein the sustained release dispenser is a pump, a gel or a membrane.

16. The composition of claim 1 wherein the composition is capable of stimulating a volatile plume-oriented upwind flight in a wind tunnel having a wind velocity of about 50 cm/second.

17. The composition of claim 16 wherein the composition is capable of stimulating an electroantennogram response from a house fly antenna.

18. A synthetic fly attractant composition comprising an effective amount of at least one ammonia-releasing compound butanoic acid, dimethyltrisulfide and indole.

19. A synthetic fly trap comprising means to retain house flies within the trap and a house fly attractant composition comprising an effective amount of at least one ammonia-releasing compound, at least one volatile short chain carboxylic acid, at least one organic sulfide, and at least one nitrogen heterocycle containing compound.

20. The trap of claim 19 wherein the ammonia-releasing compound is selected from the group consisting of ammonium carbonate, ammonium chloride, ammonia gas and ammonium sulfate.

21. The trap of claim 19 wherein the volatile short chain carboxylic acid is selected from the group consisting of butanoic acid and 3-methyl butanoic acid.

22. The trap of claim 19 wherein the organic sulfide is selected from the group of dimethyl disulfide, dimethyl trisulfide and dimethyl tetrasulfide.

23. The trap of claim 19 wherein the nitrogen heterocycle containing compound is selected from the group consisting of indole and 3-methyl indole.

24. The trap of claim 19 wherein the attractant composition comprises at least one amonia-releasing compound, butanoic acid, dimethyltrisulfide and indole.

25. The trap of claim 19 further comprising at least one additional component selected from the group consisting of volatile aromatic-containing alcohols and volatile amines that are naturally found in pig or cow manure.

26. The trap of claim 25 wherein the at least one additional component is selected from the group consisting of phenol, benzeneethanol, and trimethylamine.

27. The trap of claim 19 wherein the attractant composition is provided in a sustained release dispenser.

28. The trap of claim 27 wherein the sustained release dispenser is a pump, a gel or a membrane.

29. The trap of claim 19 wherein the means to retain flies is a tacky surface, an insecticide, a trap box, electrocution, or liquid.

30. The trap of claim 19 wherein the trap additionally comprises a heat stimuli.

31. The trap of claim 19 wherein the trap additionally comprises a visual stimuli.

32. The trap of claim 31 wherein the visual stimuli is light.

33. The trap of claim 32 wherein the visual stimuli is UV light.

34. A method for attracting house flies comprising the steps of:

preparing a synthetic composition comprising at least one ammonia-releasing compound, at least one volatile short chain carboxylic acid, at least one organic sulfide, and at least one nitrogen heterocycle containing compound; and positioning an effective house fly attracting amount of the composition in an area where house flies are present.

35. The method of claim 34 additionally comprising the step of combining the composition with a means for retaining flies.

36. The method of claim 34 wherein the ammonia-releasing compound is selected from the group consisting of ammonium carbonate, ammonium chloride, ammonia gas and ammonium sulfate; the volatile short chain carboxylic acid is selected from the group consisting of butanoic acid and 3-methyl butanoic acid; the organic sulfide is selected from the group consisting of dimethyl disulfide, dimethyl trisulfide and dimethyl tetrasulfide; and, the nitrogen heterocycle containing compond is selected from the group consisting of indole and 3-methyl indole.

37. The method of claim 34 wherein the attractant composition comprises at least one amonia-releasing compound, butanoic acid, dimethyltrisulfide and indole.

38. The method of claim 34 wherein the attractant composition further comprises at least one additional component selected from the group consisting of volatile aromatic-containing alcohols and volatile amines that are naturally found in pig or cow manure.

39. The method of claim 34 wherein the at least one additional component is selected from the group consisting of phenol, benzeneethanol, and trimethylamine.

40. The method of claim 34 wherein the positioning step takes place in a livestock facility.

41. The method of claim 34 wherein the positioning step takes place in a residence.

42. The method of claim 34 wherein the positioning step takes place in a commercial facility.

43. The method of claim 44 wherein the commercial facility is a restaurant, a slaughterhouse, a school or a hospital.

44. The method of claim 34 wherein the attractant composition is provided in a sustained release dispenser.

45. The method of claim 44 wherein the sustained release dispenser is a pump, a gel or a membrane.

46. The method of claim 45, wherein the pump includes an atomizer or a metered aerosol canister.

47. The method of claim 35 wherein the means for retaining flies is a tacky surface, an insecticide, a trap box, electrocution or liquid.

48. A synthetic fly attractant composition comprising an effective amount of at least one ammonia-releasing compound, at least one volatile short chain carboxylic acid, at least one organic sulfide, and at least one nitrogen heterocycle containing compound wherein the volatile short chain carboxylic acid, the organic sulfide, and the nitrogen heterocycle containing compound in said synthetic house fly attracting composition are those that are naturally occurring in pig or cow manure.

49. The composition of claim 48 wherein the volatile short chain carboxylic acid is selected from the group consisting of butanoic acid and 3-methyl butanoic acid; the organic sulfide is selected from the group consisting of dimethyl disulfide, dimethyl trisulfide and dimethyl tetrasulfide; and, the nitrogen heterocycle containing compound is selected from the group of indole and 3-methyl indole.

50. The composition of claim 49 further comprising at least one additional component selected from the group consisting of benzeneethanol, phenol and trimethylamine.

51. The composition of claim 48 in a sustained release dispenser.

52. The composition of claim 51 wherein the sustained release dispenser is a pump.

53. A synthetic fly attractant composition prepared by combining an effectice amount of at least one ammonia-releasing compound, at least one volatile short chain carboxylic acid, at least one organic sulfide, and at least one nitrogen heterocycle containing compound wherein the composition is capable of stimulating an electroantennogram response from a house fly antenna.

54. The composition of claim 53, wherein the composition is capable of stimulating a volatile plume-oriented upwind flights in flies released in a wind tunnel having a wind velocity of about 50 cm/second.

* * * * *

UNITED STATES PATENT AND TRADEMARK OFFICE
CERTIFICATE OF CORRECTION

PATENT NO. : 6,106,821
DATED : August 22, 2000
INVENTOR(S) : Baker et al.

It is certified that error appears in the above-identified patent and that said Letters Patent is hereby corrected as shown below:

Column 4,
Line 52, after "group of dimethyl" delete "di sulfide" and replace with -- disulfide --.

Column 7,
Line 34, after "49:83-" delete "84" and replace with -- 87 --.

Column 9,
Line 25, delete "repared" and replace with -- prepared --.

Column 15,
Line 27, delete "0.00 1" and replace with -- 0.001 --.

Column 16,
Line 44, after "positioned" delete "I" and replace with -- 1 --.

Column 23,
Line 32, after "synthetic" insert -- house --.
Lines 58, 59 and 62 delete "heterocycles" and replace with -- heterocycle --.

Column 24,
Lines 18 and 21, after "synthetic" insert -- house --.
Line 35, after "group" insert -- consisting --.
Line 41, delete "amonia" and replace with -- ammonia --.

Column 25,
Line 17, delete "compond" and replace with -- compound --.
Line 20, delete "amonia" and replace with -- ammonia --.

UNITED STATES PATENT AND TRADEMARK OFFICE
CERTIFICATE OF CORRECTION

PATENT NO. : 6,106,821
DATED : August 22, 2000
INVENTOR(S) : Baker et al.

It is certified that error appears in the above-identified patent and that said Letters Patent is hereby corrected as shown below:

<u>Column 26,</u>
Lines 6 and 30, after "synthetic" insert -- house --.
Line 13, delete "occurring" and replace with -- found --.
Line 22, after "group" insert -- consisting --.
Line 31, delete "effectice" and replace with -- effective --.

Signed and Sealed this

Twenty-seventh Day of November, 2001

Attest:

*Attesting Officer*

NICHOLAS P. GODICI
*Acting Director of the United States Patent and Trademark Office*